United States Patent
Odashima et al.

(10) Patent No.: US 9,150,695 B2
(45) Date of Patent: Oct. 6, 2015

(54) PRODUCTION METHOD OF CYCLIC POLYARYLENE SULFIDE

(71) Applicant: TORAY INDUSTRIES, INC., Tokyo (JP)

(72) Inventors: Tomoyuki Odashima, Nagoya (JP); Shunsuke Horiuchi, Nagoya (JP); Naoto Kumagai, Nagoya (JP); Koji Yamauchi, Nagoya (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 14/353,204

(22) PCT Filed: Oct. 22, 2012

(86) PCT No.: PCT/JP2012/006737
§ 371 (c)(1),
(2) Date: Apr. 21, 2014

(87) PCT Pub. No.: WO2013/061561
PCT Pub. Date: May 2, 2013

(65) Prior Publication Data
US 2014/0256907 A1     Sep. 11, 2014

(30) Foreign Application Priority Data

Oct. 24, 2011  (JP) .................................. 2011-232778
Nov. 30, 2011  (JP) .................................. 2011-262087
Feb. 23, 2012  (JP) .................................. 2012-037527
May 28, 2012  (JP) .................................. 2012-120662
May 30, 2012  (JP) .................................. 2012-122623

(51) Int. Cl.
*C08G 75/00*     (2006.01)
*C08G 75/14*     (2006.01)
*C07D 341/00*    (2006.01)
*C08G 75/02*     (2006.01)

(52) U.S. Cl.
CPC ............. *C08G 75/14* (2013.01); *C07D 341/00* (2013.01); *C08G 75/02* (2013.01)

(58) Field of Classification Search
CPC ............... C08G 75/14; C08G 75/0259; C08G 75/0281; C08F 6/28
USPC .......... 525/537, 535; 528/373, 388, 488, 489, 528/499, 389
See application file for complete search history.

(56) References Cited

U.S. PATENT DOCUMENTS

| 3,919,177 | A | 11/1975 | Campbell |
| 5,869,599 | A | 2/1999 | Hay et al. |
| 2010/0137531 | A1 | 6/2010 | Horiuchi |
| 2012/0178898 | A1 | 7/2012 | Unohara et al. |

FOREIGN PATENT DOCUMENTS

| EP | 1 927 615 A1 | 6/2008 | |
| EP | 2 116 562 A1 | 11/2009 | |
| EP | 2116562 | 11/2009 | |
| JP | 3200027 B2 | 8/2001 | |
| JP | 2007-231255 A | 9/2007 | |
| JP | 2008-201885 A | 9/2008 | |
| JP | 2009-30012 | 2/2009 | |
| JP | 2009-149863 | 7/2009 | |
| JP | 2009-185143 A | 8/2009 | |
| JP | 2009-227952 | 10/2009 | |
| JP | 2009-227972 A | 10/2009 | |
| JP | 2010-037550 A | 2/2010 | |
| JP | 2010-095715 | * 4/2010 | ............. C08G 75/02 |
| JP | 2010-095715 A | 4/2010 | |
| JP | 2011-068885 | 4/2011 | |
| JP | 2011-068885 A | 4/2011 | |
| JP | 2011-149014 A | 8/2011 | |
| WO | WO 2008/105438 A1 | 4/2008 | |
| WO | WO 2011/024879 A1 | 3/2011 | |

OTHER PUBLICATIONS

Bull, Acad. Sci., vol. 39, p. 763-766, 1990.
International Search Report for International Application No. PCT/JP2012/006737 dated Jan. 22, 2013.
Chinese Office Action mailed Dec. 8, 2014 for Chinese Application No. 201280051622.6.

* cited by examiner

*Primary Examiner* — Shane Fang
(74) *Attorney, Agent, or Firm* — RatnerPrestia

(57) ABSTRACT

There is provided a production method of a cyclic polyarylene sulfide from a reaction mixture including at least a sulfidizing agent (a), a dihalogenated aromatic compound (b) and an organic polar solvent (c). The production method includes: a process 1 of heating the reaction mixture having an arylene unit of not less than 0.80 mol but less than 1.05 mol per 1 mol of the sulfur content in the reaction mixture; and subsequent to the process 1, a process 2 of further causing the reaction to proceed after addition of the dihalogenated aromatic compound (b) to have the arylene unit of not less than 1.05 mol and not greater than 1.50 mol per 1 mol of the sulfur content in the reaction mixture.

12 Claims, No Drawings

US 9,150,695 B2

PRODUCTION METHOD OF CYCLIC POLYARYLENE SULFIDE

CROSS REFERENCE TO RELATED APPLICATIONS

This is the U.S. National Phase application of PCT International Application No. PCT/JP2012/006737, filed Oct. 22, 2012, and claims priority to Japanese Patent Application No. 2011-232778, filed Oct. 24, 2011, Japanese Patent Application No. 2011-262087, filed Nov. 30, 2011, Japanese Patent Application No. 2012-037527, filed Feb. 23, 2012, Japanese Patent Application No. 2012-120662, filed May 28; 2012 and Japanese Patent Application No. 2012-122623, filed May 30, 2012, the disclosures of each of these applications being incorporated herein by reference in their entireties for all purposes.

FIELD OF THE INVENTION

The present invention relates to a production discloses a cyclic polyarylene sulfide. More specifically the invention discloses a method of producing a cyclic polyarylene sulfide by reaction under heating of a reaction product including at least a sulfidizing agent, a dihalogenated aromatic compound and an organic polar solvent, which allows for production of high purity cyclic polyarylene sulfide with a high efficiency by a simple technique.

BACKGROUND OF THE INVENTION

Cyclic aromatic compounds have recently received attention, because of the characteristics derived from their cyclic structure, i.e., their structure-derived specificity. More specifically, the cyclic aromatic compounds have potential for development in applications of high-performance materials or functional materials and are expected to be used as inclusion compounds or to be used as effective monomers for syntheses of high molecular-weight linear polymers by ring-opening polymerization. Cyclic polyarylene sulfide (hereinafter polyarylene sulfide may be abbreviated as PAS) is a remarkable compound belonging to the category of cyclic aromatic compounds.

A proposed production method of cyclic polyarylene sulfide is, for example, a method of oxidative polymerization of a diaryl disulfide compound under an ultra dilute condition (for example, Patent Document 1). This method is expected to produce cyclic polyarylene sulfide at high selectivity and produce only a very low amount of linear polyarylene sulfide, and actually allows for production of cyclic polyarylene sulfide at a high yield. This method, however, requires the reaction under the ultra dilute condition and accordingly produces a very little amount of cyclic polyarylene sulfide per unit volume of a reaction vessel. This method accordingly has many problems in terms of producing cyclic polyarylene sulfide with high efficiency. This method has the reaction temperature of about room temperature and thus requires a long time of several ten hours for the reaction. This method accordingly has low productivity. Additionally, linear polyarylene sulfide produced as a byproduct by this method has low molecular weight including disulfide bond derived from diaryl disulfide as the raw material and low thermal stability and is practically not valuable. The linear polyarylene sulfide produced as the byproduct by this method has molecular weight similar to the molecular weight of the cyclic polyarylene sulfide as the objective substance, so that it is difficult to separate the cyclic polyarylene sulfide from the linear polyarylene sulfide as the byproduct. This method accordingly has extreme difficulty in production of high purity cyclic polyarylene sulfide with high efficiency. Additionally, this method requires an equal amount of an expensive oxidizing agent such as dichlorodicyanobenzoquinone to the amount of diaryl disulfide used as the raw material for the progress of oxidative polymerization. This method is thus not capable of producing cyclic polyarylene sulfide at a low cost. Another proposed method of oxidative polymerization of the diaryl disulfide compound under an ultra dilute condition performs oxidative polymerization in the presence of a metal catalyst and uses oxygen as the oxidizing agent. This method uses the inexpensive oxidizing agent but still has many problems, for example, difficulty in control of the reaction to produce a variety of and a large amount of oligomers and an extremely long time required for the reaction. In any case, the method of oxidative polymerization of the diaryl disulfide compound under the ultra dilute condition is not capable of producing high purity cyclic polyarylene sulfide at a low cost and with high efficiency.

Another proposed production method of cyclic polyarylene sulfide is a method of heating a copper salt of 4-bromothiophenol in quinoline under an ultra dilute condition. Like the above method of Patent Document 1, this method also requires the ultra dilute condition and a long time for the reaction and accordingly has extremely low productivity. Additionally this method has difficulty in separating copper bromide as a byproduct from cyclic polyarylene sulfide as an objective product and allows for production of only low purity cyclic polyarylene sulfide (for example, Patent Document 2).

A method disclosed to manufacture cyclic polyarylene sulfide at a high yield from general raw materials is a method of reacting a sulfidizing agent and a dihalogenated aromatic compound in 1.25 liters or more of an organic polar solvent relative to 1 mol of sulfur content in the sulfidizing agent (for example, Patent Document 3). This method, however, has only a low yield of cyclic polyarylene sulfide relative to the raw material monomer and produces a large amount of linear polyarylene sulfide as a byproduct. There is accordingly a need for improvement.

A method disclosed to produce cyclic polyarylene sulfide at a high yield is a method of exposing a dihalogenated aromatic compound such as 1,4-bis-(4'-bromophenylthio) benzene to sodium sulfide in N-methylpyrrolidone under reflux temperature (for example, Non-Patent Document 1). This method is expected to obtain cyclic polyarylene sulfide, since the volume of the organic polar solvent per 1 mol of sulfur content in the reaction mixture is 1.25 liters or more. This method, however, does not use linear polyarylene sulfide as the raw material and thus needs to use a large amount of a dihalogenated aromatic compound. This method also uses a very special compound as the dihalogenated aromatic compound and is thus industrially of little practical use. There is accordingly a need for improvement.

A method disclosed to solve the above problems is a method of heating and reacting a linear polyarylene sulfide, a sulfidizing agent and a dihalogenated aromatic compound in 1.25 liters or more of an organic polar solvent relative to 1 mol of sulfur content in the reaction mixture (for example, Patent Document 4). This method uses linear polyarylene sulfide as the raw material and thus reduces the amount of monomer used and improves the yield of cyclic polyarylene sulfide relative to the monomer. The method is accordingly expected to be industrially practical. This method has, however, been examined only for the procedure of simultaneously feeding and reacting all the reaction raw materials, i.e., linear polyarylene sulfide, a sulfidizing agent, a dihalogenated aromatic compound and an organic polar solvent. There have been no reviews for improvement of the yield and the formation rate of cyclic polyarylene sulfide and reduction of the impurity content by supplementary addition of the dihalogenated aromatic compound that is a preferred characteristic of the invention.

A disclosed multi-stage production method of cyclic polyarylene sulfide accompanied with supplementary addition of a dihalogenated aromatic compound is a method of performing a reaction (A) of heating a reaction mixture including linear polyarylene sulfide, a sulfidizing agent, an organic polar solvent and less than 0.9 mol of a dihalogenated aromatic compound relative to 1 mol of sulfur content in the sulfidizing agent and a reaction (B) of supplementary adding the dihalogenated aromatic compound and heating the reaction mixture in 1.25 liters or more of the organic polar solvent relative to 1 mol of sulfur content in the reaction mixture (for example, Patent Document 5). This method is characterized by cyclization of a low molecular-weight prepolymer obtained in the reaction (A) by supplementary addition of the dihalogenated aromatic compound in the reaction (B). In order to produce the prepolymer with high efficiency, it is preferable that substantially no dihalogenated aromatic compound is present in the reaction mixture in the reaction (A). Actually, only the method including no dihalogenated aromatic compound in the reaction (A) has been examined conventionally. In order to produce the prepolymer with high efficiency, it is also preferable that the volume of the organic polar solvent in the reaction mixture in the reaction (A) is less than 1.25 liters per 1 mol of sulfur content. Actually, only the method using 1 liter of the organic polar solvent in the reaction mixture per 1 mol of sulfur content has been examined conventionally. The effects on the yield have accordingly been unknown in manufacture of cyclic polyarylene sulfide in positive coexistence of a dihalogenated aromatic compound in the reaction mixture prior to supplementary addition of the dihalogenated aromatic compound under a diluter condition that the volume of the organic polar solvent is 1.25 liters or more per 1 mol of sulfur content through the entire reaction process.

The methods disclosed in Patent Documents 3 and 4 for recovery of cyclic polyarylene sulfide first recover a solid mixture mainly consisting of cyclic polyarylene sulfide and linear polyarylene sulfide by removal of part or most part of the organic polar solvent from a reaction mixture obtained by the reaction, subsequently expose the recovered solid mixture to a solvent that is capable of dissolving the cyclic polyarylene sulfide to prepare a solution including the cyclic polyarylene sulfide and remove the solvent used for dissolution from the solution, so as to obtain the cyclic polyarylene sulfide.

A method disclosed to produce high purity cyclic polyarylene sulfide similar to the above recovery method exposes a polyarylene sulfide mixture including at least linear polyarylene sulfide and cyclic polyarylene sulfide to a solvent that is capable of dissolving the cycling polyarylene sulfide to prepare a solution including the cyclic polyarylene sulfide and subsequently obtains the cyclic polyarylene sulfide from the solution (for example, Patent Document 6). These methods ensure production of high purity cyclic polyarylene sulfide. In order to produce the high purity cyclic polyarylene sulfide, however, the method requires the process of preparing a reaction mixture consisting of cyclic polyarylene sulfide, linear polyarylene sulfide and an organic polar solvent, the process of removing the organic polar solvent from the reaction mixture to produce a solid mixture including the cyclic polyarylene sulfide and the linear polyarylene sulfide, the process of exposing the solid mixture to a solvent to obtain a solution including the cyclic polyarylene sulfide and the process of removing the solvent from this solution. The procedure is thus rather troublesome.

A method disclosed to solve the above problems in recovery of cyclic polyarylene sulfide or more specifically to recover high purity cyclic polyarylene sulfide with high efficiency by a simple technique is a recovery method of cyclic polyarylene sulfide from a reaction mixture, which is characterized by removal of an organic polar solvent from a filtrate obtained by solid-liquid separation of the reaction mixture in a temperature range of not higher than the boiling point of the organic polar solvent under ordinary pressure, wherein the reaction mixture is obtained by exposure and reaction of at least a sulfidizing agent and a dihalogenated aromatic compound in the organic polar solvent and includes at least linear polyarylene sulfide and cyclic polyarylene sulfide (for example, Patent Document 7). Another disclosed method is a method of distilling out part of an organic polar solvent from a mixture including at least polyarylene sulfide, cyclic polyarylene sulfide and the organic polar solvent and subsequently recovering the cyclic polyarylene sulfide by solid-liquid separation (for example, Patent Document 8). These methods separate and recover cyclic polyarylene sulfide as the objective substance by the simple technique of solid-liquid separation. These are expected to improve the above problems of the prior arts. These methods, however, do not perform supplementary addition of a dihalogenated aromatic compound and further reaction, which are preferred characteristics of the invention, in the process of obtaining the reaction product including cyclic polyarylene sulfide. Accordingly, there is still a problem that a long separation time is required in the process of solid-liquid separation of the reaction product. Additionally, the resulting cyclic polyarylene sulfide has not sufficiently high purity. Further improvement is thus needed.

PATENT DOCUMENTS

Patent Document 1: JP 3200027B
Patent Document 2: U.S. Pat. No. 5,869,599
Patent Document 3: JP 2009-30012A
Patent Document 4: WO 2008/105438
Patent Document 5: JP 2011-068885A
Patent Document 6: JP 2007-231255A
Patent Document 7: JP 2009-149863A
Patent Document 8: JP 2010-037550A
Non-Patent Document: Bull, Acad. Sci., vol., 39, p. 763-766, 1990

SUMMARY OF THE INVENTION

In order to solve the above problems of the prior art, the invention aims to provide a method of efficiently producing a high purity cyclic polyarylene sulfide by a simple technique.

The present invention is accordingly made to solve at least part of the problems described above and may be implemented by the following aspects.

1. There is provided a production method of a cyclic polyarylene sulfide by a reaction of a reaction mixture under heating, wherein the reaction mixture includes at least a sulfidizing agent (a), a dihalogenated aromatic compound (b) and an organic polar solvent (c), the reaction mixture having the organic polar solvent (c) of not less than 1.25 liters and not more than 50 liters relative to 1 mol of sulfur content in the reaction mixture. The production method comprises:

a process 1 of heating the reaction mixture having an arylene unit of not less than 0.80 mol but less than 1.05 mol per 1 mol of the sulfur content in the reaction mixture and thereby causing the reaction to proceed until 50% or more of the sulfidizing agent (a) in the reaction mixture is consumed for the reaction; and subsequent to the process 1, a process 2 of further causing the reaction to proceed under heating after addition of the dihalogenated aromatic compound (b) to have the arylene unit of not less than 1.05 mol and not greater than 1.50 mol per 1 mol of the sulfur content in the reaction mixture, so as to obtain a reaction product including at least a cyclic polyarylene sulfide and a linear polyarylene sulfide.

2. There is provided the production method of the cyclic polyarylene sulfide according to aspect 1, further comprising: subsequent to the process 2, a process 3 of performing solid-liquid separation of the reaction product in a temperature range of not higher than a boiling point of the organic polar solvent (c) under ordinary pressure, so as to obtain a filtrate including the cyclic polyarylene sulfide and the organic polar solvent (c).

3. There is provided the production method of the cyclic polyarylene sulfide according to either one of aspects 1 and 2, wherein the process 1 heats the reaction mixture having the arylene unit of not less than 0.80 mol but less than 1.00 mol per 1 mol of the sulfur content in the reaction mixture.

4. There is provided the production method of the cyclic polyarylene sulfide according to any one of aspects 1 to 3, wherein the reaction mixture further includes a linear polyarylene sulfide (d).

5. There is provided the production method of the cyclic polyarylene sulfide according to aspect 4, wherein the reaction mixture includes the linear polyarylene sulfide (d) at a start of the reaction in the process 1.

6. There is provided the production method of the cyclic polyarylene sulfide according to any one of aspects 1 to 5, wherein the process 2 is performed after the reaction proceeds until 70% or more of the sulfidizing agent (a) in the reaction mixture is consumed for the reaction in the process 1.

7. There is provided the production method of the cyclic polyarylene sulfide according to any one of aspects 1 to 6, wherein the process 1 is performed using the reaction mixture containing 0.2 to 20.0 mol of water per 1 mol of the sulfur content in the reaction mixture.

8. There is provided the production method of the cyclic polyarylene sulfide according to any one of aspects 1 to 7, wherein the reaction mixture is heated at a temperature exceeding a reflux temperature of the reaction mixture under ordinary pressure in the process 1 and in the process 2.

9. There is provided the production method of the cyclic polyarylene sulfide according to any one of aspects 1 to 8, wherein a pressure in heating the reaction mixture is equal to or more than 0.05 MPa as a gauge pressure in the process 1 and in the process 2.

10. There is provided the production method of the cyclic polyarylene sulfide according to any one of aspects 1 to 9, wherein the dihalogenated aromatic compound (b) is dichlorobenzene.

11. There is provided the production method of the cyclic polyarylene sulfide according to any one of aspects 1 to 10, wherein the sulfidizing agent (a) is an alkali metal sulfide.

12. There is provided the production method of the cyclic polyarylene sulfide according to either one of aspects 4 and 5, wherein the linear polyarylene sulfide (d) used is a linear polyarylene sulfide obtained by separation of a cyclic polyarylene sulfide from a polyarylene sulfide mixture including a cyclic polyarylene sulfide and a linear polyarylene sulfide, wherein the polyarylene sulfide mixture is obtained by a reaction under heating of a reaction mixture, wherein the reaction mixture includes at least a sulfidizing agent (a), a dihalogenated aromatic compound (b) and an organic polar solvent (c) and the reaction mixture has the organic polar solvent (c) of not less than 1.25 liters and not more than 50 liters relative to 1 mol of sulfur content in the reaction mixture, by a method comprising:

a process 1 of heating the reaction mixture having an arylene unit of not less than 0.80 mol but less than 1.05 mol per 1 mol of the sulfur content in the reaction mixture and thereby causing the reaction to proceed until 50% or more of the sulfidizing agent (a) in the reaction mixture is consumed for the reaction; and subsequent to the process 1, a process 2 of further causing the reaction to proceed under heating after addition of the dihalogenated aromatic compound (b) to have the arylene unit of not less than 1.05 mol and not greater than 1.50 mol per 1 mol of the sulfur content in the reaction mixture, so as to obtain a reaction product including at least a cyclic polyarylene sulfide and a linear polyarylene sulfide.

13. There is provided the production method of the cyclic polyarylene sulfide according to either one of aspects 4 and 5, wherein the linear polyarylene sulfide (d) used is a linear polyarylene sulfide obtained by separation of a cyclic polyarylene sulfide from a polyarylene sulfide mixture including a cyclic polyarylene sulfide and a linear polyarylene sulfide, wherein the polyarylene sulfide mixture is obtained by a reaction under heating of a reaction mixture, wherein the reaction mixture includes at least a linear polyarylene sulfide (d), a sulfidizing agent (a), a dihalogenated aromatic compound (b) and an organic polar solvent (c) and the reaction mixture has the organic polar solvent (c) of not less than 1.25 liters and not more than 50 liters relative to 1 mol of sulfur content in the reaction mixture, by a method comprising:

a process 1 of heating the reaction mixture having an arylene unit of not less than 0.80 mol but less than 1.05 mol per 1 mol of the sulfur content in the reaction mixture and thereby causing the reaction to proceed until 50% or more of the sulfidizing agent (a) in the reaction mixture is consumed for the reaction; and subsequent to the process 1, a process 2 of further causing the reaction to proceed under heating after addition of the dihalogenated aromatic compound (b) to have the arylene unit of not less than 1.05 mol and not greater than 1.50 mol per 1 mol of the sulfur content in the reaction mixture, so as to obtain a reaction product including at least a cyclic polyarylene sulfide and a linear polyarylene sulfide.

The present invention provides a method of efficiently producing a high purity cyclic polyarylene sulfide by a simple technique.

DETAILED DESCRIPTION OF EMBODIMENTS OF THE INVENTION

The following describes embodiments of the invention in detail. The embodiments of the invention relate to the production method of a cyclic polyarylene sulfide (hereinafter may be abbreviated as cyclic PAS).

(1) Sulfidizing Agent

The sulfidizing agent used according to an embodiment of the invention may be any sulfidizing agent that introduces a sulfide bond into a dihalogenated aromatic compound and affects an arylene sulfide bond to produce arylene thiolate and may be, for example, an alkali metal sulfide, an alkali metal hydrosulfide or hydrogen sulfide.

Specific examples of the alkali metal sulfide include lithium sulfide, sodium sulfide, potassium sulfide, rubidium sulfide, cesium sulfide and mixtures of two or more of these alkali metal sulfides. Among them, lithium sulfide and/or sodium sulfide are preferably used, and sodium sulfide is more preferably used. Any of these alkali metal sulfides may be used as a hydrate or an aqueous mixture or in the form of an anhydride. The aqueous mixture herein indicates an aqueous solution, a mixture of an aqueous solution and a solid component or a mixture of water and a solid component. Commonly available, inexpensive alkali metal sulfides are in the form of hydrates or aqueous mixtures, so that it is preferable to use an alkali metal sulfide in such a form.

Specific examples of the alkali metal hydrosulfide include lithium hydrosulfide, sodium hydrosulfide, potassium hydrosulfide, lithium hydrosulfide, rubidium hydrosulfide, cesium hydrosulfide and mixtures of two or more of these alkali metal hydrosulfides. Among them, lithium hydrosulfide and/or sodium hydrosulfide are preferably used, and sodium hydrosulfide is more preferably used.

An alkali metal sulfide produced in a reaction system of an alkali metal hydrosulfide and an alkali metal hydroxide may also be used. An alkali metal sulfide prepared in advance by exposure of an alkali metal hydrosulfide to an alkali metal hydroxide may also be used. Any of these alkali metal hydrosulfides and alkali metal hydroxides may be used in the form of a compound selected among a hydrate, an aqueous mixture and an anhydride. The hydrate or the aqueous mixture is preferable in terms of the availability and the cost.

Additionally, an alkali metal sulfide produced in a reaction system of an alkali metal hydroxide such as lithium hydroxide or sodium hydroxide and hydrogen sulfide may be used. An alkali metal sulfide prepared in advance by exposure of an alkali metal hydroxide such as lithium hydroxide or sodium hydroxide to hydrogen sulfide may also be used. Hydrogen sulfide may be used in any of gas form, liquid form and aqueous solution form.

In the case that there is a partial loss of the sulfidizing agent by, for example, dehydration operation prior to start of the reaction with the dihalogenated aromatic compound, the amount of the sulfidizing agent according to the invention means a remaining amount by subtraction of the loss from an actual amount added as the raw material.

An alkali metal hydroxide and/or an alkaline earth metal hydroxide may be used in combination with the sulfidizing agent. Preferable examples of the alkali metal hydroxide specifically include sodium hydroxide, potassium hydroxide, lithium hydroxide, rubidium hydroxide, cesium hydroxide and mixtures of two or more of these alkali metal hydroxides. Specific examples of the alkaline earth metal hydroxide include calcium hydroxide, strontium hydroxide and barium hydroxide. Among them, sodium hydroxide is preferably used.

When the alkali metal hydrosulfide is used as the sulfidizing agent, it is especially preferable to use an alkali metal hydroxide simultaneously. In this case, the used amount of the alkali metal hydroxide is, for example, equal to or more than 0.95 mol, is preferably equal to or more than 1.00 mol and is more preferably equal to or more than 1.005 mol per 1 mol of the alkali metal hydrosulfide. The used amount of the alkali metal hydroxide is also, for example, equal to or less than 1.50 mol, is preferably equal to or less than 1.25 mol and is more preferably equal to or less than 1.200 mol. When hydrogen sulfide is used as the sulfidizing agent, it is especially preferable to use an alkali metal hydroxide simultaneously. In this case, the used amount of the alkali metal hydroxide is, for example, equal to or more than 2.0 mol, is preferably equal to or more than 2.01 mol and is more preferably equal to or more than 2.04 mol per 1 mol of hydrogen sulfide. The used amount of the alkali metal hydroxide is also, for example, equal to or less than 3.0 mol, is preferably equal to or less than 2.50 mol and is more preferably equal to or less than 2.40 mol.

(2) Dihalogenated Aromatic Compound

The dihalogenated aromatic compound used according to an exemplary embodiment of the invention is an aromatic compound having an arylene group that is a divalent aromatic ring group and two halogeno groups. One mole of the dihalogenated aromatic compound has one mole of the arylene unit and two moles of the halogeno group. Examples of a compound having a phenylene group that is a divalent benzene ring group as the arylene group and two halogeno groups include dihalogenated benzenes such as p-dichlorobenzene, o-dichlorobenzene, m-dichlorobenzene, p-dibromobenzene, o-dibromobenzene, m-dibromobenzene, 1-bromo-4-chlorobenzene and 1-bromo-3-chlorobenzene. Other examples of the dihalogenated aromatic compound include compounds having additional substituents other than halogens, such as 1-methoxy-2,5-dichlorobenzene, 1-methyl-2,5-dichlorobenzene, 1,4-dimethyl-2,5-dichlorobenzene, 1,3-dimethyl-2,5-dichlorobenzene and 3,5-dichlorobenzoic acid. Among them, preferable are dihalogenated aromatic compounds including p-dihalogenated benzene as the primary component, such as p-dichlorobenzene. Especially preferable is a dihalogenated aromatic compound including 80 to 100 mol % of p-dichlorobenzene, and more preferable is a dihalogenated aromatic compound including 90 to 100 mol % of p-dichlorobenzene. Two or more different dihalogenated aromatic compounds may be used in combination, in order to obtain a cyclic PAS copolymer.

(3) Linear Polyarylene Sulfide

A linear polyarylene sulfide (hereinafter may be abbreviated as linear PAS) according to an exemplary embodiment of the invention is a linear homopolymer or a linear copolymer including a repeating unit of —(Ar—S)— as the main constituent unit and preferably containing 80 mol % or more of this repeating unit. Available examples of Ar include units shown by the following formula (A) to formula (L). Among them, the unit of formula (A) is especially preferable.

[Chem. 1]

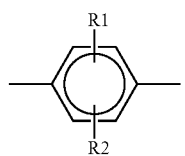
(A)

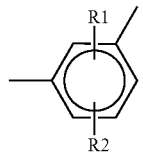
(B)

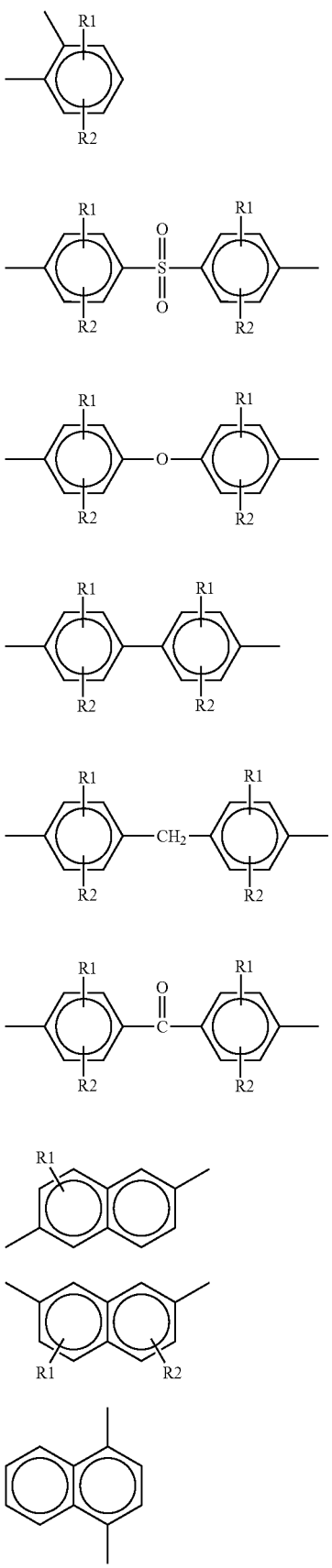

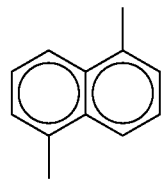

(wherein R1 and R2 in formulae represent substituents selected among hydrogen, alkyl groups containing one to six carbon atoms, alkoxy groups containing one to six carbon atoms and halogen groups, wherein R1 and R2 may be identical or may be different).

The linear polyarylene sulfide including this repeating unit as the main constituent unit may additionally include a small amount of a branch unit or a cross-linking unit shown by any of the following formula (M) to formula (P). The copolymerization amount of this branch unit or cross-linking unit is preferably in the range of 0 to 1 mol % relative to 1 mol of the main constituent unit expressed by —(Ar—S)—.

[Chem. 2]

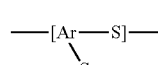 (M)

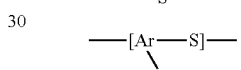 (N)

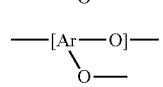 (O)

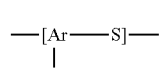 (P)

The linear PAS according to an exemplary embodiment of the invention may be any of random copolymers, block copolymers and mixtures thereof including the repeating unit described above.

Typical examples of the linear PAS include polyphenylene sulfides, polyphenylene sulfide sulfones, polyphenylene sulfide ketones, their random copolymers, their block copolymers and mixtures thereof. Especially preferable examples of the linear PAS are polyphenylene sulfides (hereinafter may be abbreviated as PPS), polyphenylene sulfide sulfones and polyphenylene sulfide ketones containing 80 mol % or more of or preferably 90 mol % or more of the following p-phenylene sulfide unit as the main constituent unit of the polymer:

[Chem. 3]

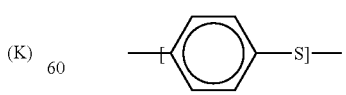

In the production method of the cyclic PAS according to an exemplary embodiment of the invention, the linear PAS may be used as the raw material. The melt viscosity of the linear PAS used in this application is not specifically limited but may be in the range of 0.1 to 1000 Pa·s (300° C., shear rate of 1000/second) as the melt viscosity of common linear PAS and more specifically in the range of 0.1 to 500 Pa·s. The molecular weight of the linear PAS is also not specifically limited, but common PAS may be used as the linear PAS. The weight-average molecular weight of such PAS is equal to or more than 5,000, is preferably equal to or more than 7,500 and is more preferably equal to or more than 10,000. The weight-average molecular weight of the PAS is also equal to or less than 1,000,000, is preferably equal to or less than 500,000 and is more preferably equal to or less than 100,000. In general, the lower weight-average molecular weight increases the solubility in an organic polar solvent and thereby advantageously reduces the time required for the reaction. The linear PAS having the weight-average molecular weight of the above range is usable without causing any substantive problem.

The production method of such linear PAS is not specifically limited, but the linear PAS used may be produced by any manufacturing process. For example, the linear PAS may be manufactured by reaction of an aromatic compound containing at least one nucleus-substituted halogen or thiophene with an alkali metal sulfide in a polar organic solvent at a raised temperature as described in, for example, JP S45-3368B, S52-12240B and S63-3375B. The linear PAS may be manufactured preferably by exposure of a dihalogenated aromatic compound to a sulfidizing agent in an organic polar solvent as described in, for example, JP H05-163349A. Molded products using the PAS manufactured by any of these methods and molding waste, as well as waste plastics derived from the PAS manufactured by any of these methods and off-specification products may also extensively be used as the linear PAS.

A cyclic compound is generally manufactured by competing reactions of producing a cyclic compound and producing a linear compound. In a method for producing a cyclic polyarylene sulfide, a considerable amount of a linear polyarylene sulfide is accordingly produced as a byproduct, other than the cyclic polyarylene sulfide as the objective substance. The invention preferably enables this linear polyarylene sulfide obtained as the byproduct to be used as the raw material without any difficulty. For example, an especially preferable process uses, as the raw material, a linear polyarylene sulfide obtained by separation of a cyclic polyarylene sulfide from a resulting polyarylene sulfide mixture including the cyclic polyarylene sulfide and the linear polyarylene sulfide by the aforementioned production method of cyclic PAS described in, for example, Patent Document 3, i.e., the production method by the reaction under heating of a sulfidizing agent and a dihalogenated aromatic compound using an organic polar solvent of 1.25 liters or more relative to 1 mol of the sulfur content in the sulfidizing agent. Another preferable process uses, as the raw material, a linear polyarylene sulfide obtained by separation of a cyclic polyarylene sulfide from a resulting polyarylene sulfide mixture including the cyclic polyarylene sulfide and the linear polyarylene sulfide by the aforementioned production method of cyclic PAS described in, for example, Patent Document 4, i.e., the production method by the reaction under heating of a linear polyarylene sulfide, a sulfidizing agent and a dihalogenated aromatic compound using an organic polar solvent of 1.25 liters or more relative to 1 mol of the sulfur content in the reaction mixture.

Additionally, in the production method of a cyclic polyarylene sulfide by the reaction under heating of a reaction mixture including at least a linear polyarylene sulfide (d), a sulfidizing agent (a), a dihalogenated aromatic compound (b) and an organic polar solvent (c) and more specifically including the organic polar solvent (c) of not less than 1.25 liters and not greater than 50 liters relative to 1 mol of the sulfur content in the reaction mixture, the reaction mixture having the arylene unit of not less than 0.80 mol but less than 1.05 mol per 1 mol of the sulfur content in the reaction mixture is subjected to the reaction under heating (Process 1). Subsequent to Process 1, the reaction further proceeds after addition of the dihalogenated aromatic compound (b) such that the reaction mixture includes the arylene unit of not less than 1.05 mol and not greater than 1.50 mol per 1 mol of the sulfur content in the reaction mixture. A furthermore preferable process uses a linear polyarylene sulfide obtained by separation of a cyclic polyarylene sulfide from a resulting polyarylene sulfide mixture including the cyclic polyarylene sulfide and the linear polyarylene sulfide by this further reaction.

In production of a cyclic compound, e.g., a cyclic polyarylene sulfide, a linear compound as a byproduct, e.g., a low molecular-weight linear polyarylene sulfide, is conventionally discarded as useless. Production of a cyclic compound accordingly has the problems, i.e., a large amount of waste caused by this linear compound as the byproduct and a low yield relative to the raw material monomer. The invention preferably enables the linear polyarylene sulfide as the byproduct to be used as the raw material. This is of great significance in terms of significantly reducing the amount of waste and drastically improving the yield relative to the raw material monomer.

The form of the linear polyarylene sulfide is not specifically limited, but may be powder, particle, granule or pellet in the dried state. The linear polyarylene sulfide may be used in the state that includes an organic polar solvent as the reaction solvent or may be used in the state that includes a third component that does not essentially interfere with the reaction. The third component may be, for example, an inorganic filler or an alkali metal halide. The alkali metal halide herein includes any combinations of alkali metals (i.e., lithium, sodium, potassium, rubidium and cesium) and halogens (i.e., fluorine, chlorine, bromine, iodine and astatine). Specific examples include lithium chloride, sodium chloride, potassium chloride, lithium bromide, sodium bromide, potassium bromide, lithium iodide, sodium iodide, potassium iodide and cesium fluoride. Preferable are the alkali metal halides produced by the reaction of the sulfidizing agent and the dihalogenated aromatic compound described above. Examples of the alkali metal halide produced by a combination of easily available sulfidizing agent and dihalogenated aromatic compound are lithium chloride, sodium chloride, potassium chloride, lithium bromide, sodium bromide, potassium bromide and sodium iodide. Among them, sodium chloride, potassium chloride, sodium bromide and potassium bromide are preferable, and sodium chloride is more preferable. The linear polyarylene sulfide may be used in the form of a resin composition including the inorganic filler or the alkali metal halide.

In the production method of the cyclic polyarylene sulfide according to an exemplary embodiment of the invention, the linear PAS is produced as the byproduct as described above. The melt viscosity of the linear PAS produced according to an exemplary embodiment of the invention is not specifically limited but may be in the range of 0.1 to 1000 Pa·s (300° C., shear rate of 1000/second) as the melt viscosity of common linear PAS and in the range of 0.1 to 500 Pa·s as the easily producible range. The molecular weight of the linear PAS is also not specifically limited but may be 1,000 to 1,000,000 as the weight-average molecular weight of common PAS. The weight-average molecular weight of the linear PAS produced by the production method of the cyclic polyarylene sulfide according to an exemplary embodiment of the invention is inclined to be in the range of 2,500 to 500,000 and is more inclined to be in the range of 5,000 to 100,000. The higher weight-average molecular weight generally results in the stronger expression of the characteristics of the linear PAS and is thus inclined to facilitate separation of the cyclic PAS from the linear PAS as described later. The linear PAS having the weight-average molecular weight of the above range is usable without causing any substantive problem.

(4) Organic Polar Solvent

An exemplary embodiment of the invention uses an organic polar solvent for the reaction of the sulfidizing agent and the dihalogenated aromatic compound or for solid-liquid separation of a reaction product obtained by the reaction. An organic amide solvent is preferable as this organic polar solvent. As concrete examples, N-alkyl pyrrolidones such as N-methyl-2-pyrrolidone, N-ethyl-2-pyrrolidone and N-cyclohexyl-2-pyrrolidone, caprolactams such as N-methyl-ε-caprolactam and ε-caprolactam and aprotic organic solvents such as 1,3-dimethyl-2-imidazolidinone, N,N-dimethylacetamide, N,N-dimethylformamide and hexamethylphosphoric acid triamide and mixtures thereof are preferably used, because of their high reaction stability. Among them, N-methyl-2-pyrrolidone and 1,3-dimethyl-2-imidazolidinone are preferably used.

According to an embodiment of the invention, the volume of the organic polar solvent used for the reaction of a reaction mixture including at least a sulfidizing agent, a dihalogenated aromatic compound and an organic polar solvent is not less than 1.25 liters and not greater than 50 liters relative to 1 mol of the sulfur content in the reaction mixture. The lower limit of the used volume of the organic polar solvent is preferably not less than 1.5 liters and is more preferably not less than 2 liters. The upper limit is, on the other hand, preferably not greater than 20 liters and is more preferably not greater than 15 liters. The used volume of the solvent herein is based on the volume of the solvent at ordinary temperature and pressure. The used volume of the organic polar solvent of less than 1.25 liters relative to 1 mol of the sulfur content extremely reduces the formation rate of the cyclic polyarylene sulfide produced by the reaction of the sulfidizing agent and the dihalogenated aromatic compound, while increasing the formation rate of the linear polyarylene sulfide produced as the byproduct accompanied with production of the cyclic polyarylene sulfide, thus resulting in the poor productivity of the cyclic polyarylene sulfide per unit raw material. The formation rate of the cyclic polyarylene sulfide herein means a ratio of the amount of the cyclic polyarylene sulfide actually produced by manufacture of the cyclic polyarylene sulfide to the production amount of the cyclic polyarylene sulfide on the assumption that the sulfur content included in the sulfur-containing raw material (the sulfidizing agent and the linear polyarylene sulfide when used as the raw material) used for preparation of a reaction mixture in manufacture of the cyclic polyarylene sulfide described in detail later is entirely converted to the cyclic polyarylene sulfide. The formation rate of the cyclic polyarylene sulfide equal to 100% means that the sulfur content included in the used sulfur-containing raw material is entirely converted to the cyclic polyarylene sulfide.

With regard to the formation rate of the cyclic polyarylene sulfide, the greater used volume of the organic polar solvent is preferable in terms of more efficiently converting the used sulfur-containing raw material into the objective substance (cyclic polyarylene sulfide). An extreme increase in used volume of the organic polar solvent to achieve a significantly high formation rate in manufacture of the cyclic polyarylene sulfide is, however, inclined to reduce the production amount of the cyclic PAS per unit volume of a reaction vessel and is inclined to increase the time required for the reaction. Additionally, in the case of performing an operation of isolating and recovering the cyclic polyarylene sulfide, an excessive volume of the organic polar solvent used causes an extremely small amount of the cyclic polyarylene sulfide to be produced per unit amount of the reaction product and thus makes the recovery operation difficult. The above range of the used volume of the organic polar solvent is preferable in terms of balancing the productivity and the formation rate of the cyclic polyarylene sulfide.

An extremely large volume of a solvent is often used in general manufacture of a cyclic compound, so that the preferable range of the used volume of the solvent according to the invention often fails to efficiently producing a cyclic compound. Compared with general manufacture of a cyclic compound, an exemplary embodiment of the invention enables the cyclic PAS to be obtained more efficiently even under the condition of a relatively small volume of the solvent used, i.e., when the used volume of the solvent is equal to or less than the upper limit of the above preferable range of the used volume of the solvent. This reason is not yet elucidated but may be attributed to the favorable influence of the extremely high reaction efficiency and the high consumption rate of the raw material on production of a cyclic compound since the method according to an exemplary embodiment of the invention performs the reaction at the temperature over the reflux temperature of the reaction mixture. The used volume of the organic polar solvent in the reaction mixture herein indicates an amount by subtracting the volume of the organic polar solvent discharged out of the reaction system from the volume of the organic polar solvent introduced into the reaction system.

(5) Cyclic Polyarylene Sulfide

The cyclic polyarylene sulfide according to an exemplary embodiment of the invention is a cyclic compound including the repeating unit expressed by the formula —(Ar—S)— as the main constituent unit and preferably containing 80 mol % or more of this repeating unit, such as a compound expressed by the following general formula (Q):

[Chem. 4]

(Q)

Ar herein may be a unit expressed by any of the above formula (A) to formula (L). Among them, the formula (A) to the formula (C) are preferable; the formula (A) and the formula (B) are more preferable; and the formula (A) is especially preferable.

The cyclic polyarylene sulfide may include the repeating unit of, for example, any of the above formula (A) to formula (L) in the form of a random polymer, a block polymer or a mixture thereof. Typical examples of this cyclic polyarylene sulfide are cyclic polyphenylene sulfide, cyclic polyphenylene sulfide sulfone, cyclic polyphenylene sulfide ketone, cyclic random copolymers and cyclic block copolymers including any of these cyclic polymers and their mixtures. An especially preferable cyclic polyarylene sulfide is cyclic polyphenylene sulfide containing 80 mol % or more of or more specifically 90 mol % or more of the following p-phenylene sulfide unit as the main constituent unit:

[Chem. 5]

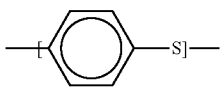

The repeating number m in the cyclic polyarylene sulfide of the above formula (Q) is not specifically limited, but a mixture having the repeating number m of 4 to 50 is preferable; a mixture having the repeating number m of 4 to 30 is more preferable; and a mixture having the repeating number m of 4 to 25 is furthermore preferable. In manufacture of a high molecular-weight polyarylene sulfide using a polyarylene sulfide prepolymer containing a cyclic polyarylene sulfide as the raw material (hereinafter the high-molecular weight polyarylene sulfide obtained from the polyarylene sulfide prepolymer as the raw material may simply be called polyarylene sulfide or PAS), it is preferable to heat this polyarylene sulfide prepolymer at the melting temperature of the polyarylene sulfide prepolymer. This enables the polyarylene sulfide to be produced efficiently.

When the repeating number m of the cyclic polyarylene sulfide is in the above range, the melting temperature of the cyclic PAS is inclined to be equal to or lower than 275° C., preferably equal to or lower than 260° C. and more preferably equal to or lower than 255° C. The melting temperature of the polyarylene sulfide prepolymer including this cyclic PAS is accordingly inclined to be lowered. The repeating number m of the cyclic PAS in the above range is preferable, since this enables the heating temperature of the polyarylene sulfide prepolymer to be lowered in manufacture of the polyarylene sulfide. The melting temperature of the cyclic PAS or the polyarylene sulfide indicates a peak temperature of an endothermic peak observed when the temperature is kept at 50° C. for 1 minute and is subsequently raised to 360° C. at a scan rate of 20° C./minute by differential scanning calorimetry.

The cyclic polyarylene sulfide according to an exemplary embodiment of the invention may be a single compound having a single repeating number or a mixture of cyclic polyarylene sulfides having different repeating numbers. The mixture of the cyclic polyarylene sulfides having the different repeating numbers is inclined to have the lower melting temperature and the less amount of heat required for melting and is thus more preferable than the single compound having the single repeating number. In the cyclic polyarylene sulfide according to an exemplary embodiment of the invention, the content rate of the cyclic PAS of the above formula (A) having m=6 to the total amount of the cyclic polyarylene sulfide is preferably less than 50% by weight, is more preferably less than 40% by weight and is furthermore preferably less than 30% by weight ([cyclic PAS of m=6 (weight)]/[cyclic PAS mixture (weight)]×100(%)). For example, Patent Document JP H10-77408A discloses a method of producing cyclohexa (p-phenylene sulfide) having the repeating number m=6 and including para-phenylene sulfide unit as Ar in the cyclic PAS. The cyclic PAS of m=6 is regarded to have a melting peak temperature at 348° C., and an extremely high processing temperature is required to process this cyclic PAS.

In manufacture of the polyarylene sulfide using the polyarylene sulfide prepolymer including the cyclic polyarylene sulfide, in terms of enabling a lower temperature to be set for the heating temperature, the cyclic PAS according to an exemplary embodiment of the invention preferably contains the cyclic PAS of the above formula (A) having m=6 in the above range. Similarly in terms of enabling a lower temperature to be set for the melt processing temperature in manufacture of the polyarylene sulfide, an exemplary embodiment of the invention preferably uses the mixture of the cyclic polyarylene sulfides having the different repeating numbers as the cyclic PAS as described above. Herein it is preferable to use a cyclic PAS mixture including 5% by weight or more of respective cyclic PASes having m=5 to 8, on the assumption that the total amount of cyclic PASes of the above formula (A) having m=4 to 13 is equal to 100% by weight among the cyclic PASes included in the cyclic PAS mixture. It is more preferable to use a cyclic PAS mixture including 7% by weight or more of respective cyclic PASes having m=5 to 8. The cyclic PAS mixture of such composition ratio is inclined to specifically reduce the melting peak temperature and the amount of melting heat and is especially preferable in terms of decreasing the melting temperature.

Herein the content rate of each of the cyclic PASes having different repeating numbers m to the total amount of the cyclic polyarylene sulfides in the cyclic PAS mixture may be determined as the ratio of a peak area attributed to a simple cyclic PAS having a desired repeating number m to a total peak area attributed to cyclic PASes in component separation of the cyclic PAS mixture by high-performance liquid chromatography using an UV detector. The respective peaks obtained in component separation by high-performance liquid chromatography are qualitatively analyzed by isolating each peak by preparative liquid chromatography and performing infrared spectroscopy for absorption spectral analysis and mass spectrometry.

(6) Production Method of Cyclic Polyarylene Sulfide

An exemplary embodiment of the invention is characterized by the following process 1 and process 2 included in manufacture of a cyclic polyarylene sulfide by the reaction under heating of a reaction mixture including at least a sulfidizing agent (a), a dihalogenated aromatic compound (b) and an organic polar solvent (c). This enables a high purity cyclic polyarylene sulfide to be efficiently obtained in a short time.

Process 1: process of heating a reaction mixture having the arylene unit of not less than 0.80 mol but less than 1.05 mol per 1 mol of the sulfur content in the reaction mixture and thereby causing the reaction to proceed until 50% or more of the sulfidizing agent (a) in the reaction mixture is consumed for the reaction.

Process 2: subsequent to the process 1, process of further causing the reaction to proceed after addition of the dihalogenated aromatic compound (b) to have the arylene unit of not less than 1.05 mol and not greater than 1.50 mol per 1 mol of the sulfur content in the reaction mixture, so as to obtain a reaction product including at least a cyclic polyarylene sulfide and a linear polyarylene sulfide.

The following describes the process 1 and the process 2 in detail.

(7) Manufacture of Cyclic Polyarylene Sulfide: Process 1

An exemplary embodiment of the invention uses a reaction mixture including the raw material components described above in the process 1. In the process 1, production of a cyclic polyarylene sulfide as the objective substance proceeds by the reaction of at least the sulfidizing agent and the dihalogenated aromatic compound included in the reaction mixture.

In the process 1, a linear polyarylene sulfide (d) may be included, in addition to the sulfidizing agent (a) and the dihalogenated aromatic compound (b), as the raw material component of the reaction mixture. In this case, production of the cyclic polyarylene sulfide as the objective substance proceeds by the reaction of the linear polyarylene sulfide in addition to the sulfidizing agent and the dihalogenated aromatic compound. Herein the linear polyarylene sulfide (d) added as the raw material component is preferably included in the reaction mixture at the start of the reaction in the process 1. This improves the production efficiency of the cyclic polyarylene sulfide. The start of the reaction herein means start of heating the reaction mixture and indicates the state of no substantial reaction consumption of the sulfidizing agent (a) and the dihalogenated aromatic compound (b). The substantial reaction consumption herein means sufficient reaction consumption of the sulfidizing agent (a) and the dihalogenated aromatic compound (b) for production of the cyclic PAS and the linear PAS having the weight-average molecular weight in the range of 2,500 to 500,000, which is likely to be produced as the byproduct by the method according to an exemplary embodiment of the invention as described above. In other words, the state of no substantial reaction consumption is not limited to the state of no reaction consumption of the sulfidizing agent (a) and the dihalogenated aromatic compound (b) but may be the state that very small amounts of the sulfidizing agent (a) and the dihalogenated aromatic compound (b) are consumed for the reaction proceeding even without heating. It is accordingly preferable that the linear polyarylene sulfide (d) is mixed with the sulfidizing agent (a), the dihalogenated aromatic compound (b) and the organic polar solvent (c) as the raw material components, prior to the process 1. There is no specific limitation in the order of or the technique of mixing these components.

The reaction mixture used in the process 1 has the arylene unit of not less than 0.80 mol but less than 1.05 mol per 1 mol of the sulfur content in the reaction mixture. The lower limit of the arylene unit described above is preferably 0.82 mol, is more preferably 0.87 mol, is furthermore preferably 0.90 mol, even more preferably 0.92 mol and is especially preferably 0.94 mol. The upper limit of the arylene unit described above is preferably 1.002 mol, is more preferably 1.005 mol, is furthermore preferably less than 1.00 mol, is even more preferably 0.995 mol and is especially preferably 0.990 mol.

Selection of the smaller value for the lower limit described above is inclined to improve the formation rate of the cyclic polyarylene sulfide as the objective substance according to an exemplary embodiment of the invention. Selection of the larger value for the lower limit is, on the other hand, inclined to reduce the production amount of impurities in manufacture of the cyclic polyarylene sulfide. Especially selection of a value of less than 0.94 mol for the lower limit is more inclined to significantly increase the formation rate of the cyclic polyarylene sulfide. Selection of a value of not less than 0.94 mol for the lower limit is, on the other hand, more inclined to remarkably suppress production of impurities. This reason is not yet elucidated but may be attributed to the influence that the amount of a reaction intermediate which is produced by the reaction in the process 1 and which is convertible into cyclic polyarylene sulfide or impurity in the process 2 subsequent to the process 1 is varied by selection of the lower limit described above. In other words, it is thought that selection of the smaller value for the lower limit described above is inclined to increase the production amount of this intermediate and thereby increase the production amount of the resulting cyclic polyarylene sulfide, while increasing the production amount of the impurities. It is also thought that selection of the larger value for the lower limit, on the other hand, is inclined to reduce the production amount of this intermediate and thereby relatively decrease the production amount of the resulting cyclic polyarylene sulfide, simultaneously with reducing the production amount of the impurities.

At the stage that the reaction of the sulfidizing agent (a) and the dihalogenated aromatic compound (b) added as the raw materials does not proceed at all, when the arylene unit-containing raw material is only the dihalogenated aromatic compound (b), the arylene unit included in the reaction mixture herein indicates the arylene unit derived from the dihalogenated aromatic compound (b) included in the reaction mixture. At the stage that the reaction proceeds or when the linear polyarylene sulfide (d) is included in the raw materials, the arylene unit included in the reaction mixture indicates the sum of the arylene unit derived from the dihalogenated aromatic compound included in the reaction mixture and the arylene unit derived from an arylene sulfide compound present in the reaction mixture.

The arylene sulfide compound according to an exemplary embodiment of the invention is produced by the reaction of the sulfidizing agent (a) with the dihalogenated aromatic compound (b) and/or the linear polyarylene sulfide (d). With progress of the reaction, the arylene sulfide unit corresponding to the consumed amount of the dihalogenated aromatic compound is newly produced. In other words, unless the arylene-containing component is removed from or added to the reaction mixture during the reaction, the amount of the arylene unit in the reaction mixture is not changed between the material feeding stage and the intermediate stage where the reaction proceeds.

The amount of the arylene unit in the reaction mixture may be determined by quantitatively determining the amount of the arylene unit derived from the dihalogenated aromatic compound and the amount of the arylene sulfide compound present in the reaction system. The amount of the dihalogenated aromatic compound in the reaction mixture may be determined by gas chromatography as described later. The amount of the arylene sulfide compound in the reaction mixture may be determined by dispersing part of the reaction mixture in a large excess of water, recovering a water-insoluble component and measuring the amount of solid content obtained by drying the recovered component.

The molar amount of the sulfur content included in the reaction mixture is synonymous with the molar amount of sulfur atom present in the reaction mixture. For example, when 1 mol of an alkali metal sulfide is present but no other sulfur-containing component is present in the reaction mixture, the amount of the sulfur content included in the reaction mixture is equal to 1 mol. As another example, when 0.5 mol of an alkali metal sulfide and 0.5 mol of the arylene sulfide unit are present in the reaction mixture, the amount of the sulfur content included in the reaction mixture is equal to 1 mol.

At the stage that the reaction of the sulfidizing agent (a) and the dihalogenated aromatic compound (b) added as the raw materials does not proceed at all, when the sulfur atom-containing raw material is only the sulfidizing agent (a), the molar amount of the sulfur content included in the reaction mixture indicates the molar amount of the sulfur content derived from the sulfidizing agent (a). At the stage that the reaction proceeds or when the linear polyarylene sulfide (d) is included in the raw materials, the molar amount of the sulfur content included in the reaction mixture indicates the total molar amount of the sulfur content derived from the sulfidizing agent included in the reaction mixture and the sulfur content derived from the arylene sulfide compound present in the reaction system.

As mentioned above, the arylene sulfide compound according to an exemplary embodiment of the invention is produced by the reaction of the sulfidizing agent (a) with the dihalogenated aromatic compound (b) and/or the linear polyarylene sulfide (d). With progress of the reaction, the arylene sulfide unit corresponding to the consumed amount of the sulfidizing agent is newly produced. In other words, unless the sulfidizing agent is removed or lost from or added to the reaction mixture during the reaction, the amount of the sulfur content included in the reaction mixture is not changed between the material feeding stage and the intermediate stage where the reaction proceeds.

The amount of the sulfur content in the reaction mixture may be determined by quantitatively determining the amount of the sulfur content derived from the sulfidizing agent and the amount of the arylene sulfide compound present in the reaction system. The amount of the sulfidizing agent in the reaction mixture may be determined by ion chromatography as described later. The method of quantitatively determining the arylene sulfide compound in the reaction mixture is described previously.

Setting the amount of the arylene unit per 1 mol of the sulfur content in the reaction mixture to the range described previously, i.e., the range of not less than 0.80 mol but less than 1.05 mol, in the process 1 is of significant importance, in order to enhance the formation rate and the quality of the resulting cyclic polyarylene sulfide. When the amount of the arylene unit per 1 mol of the sulfur content in the reaction mixture is less than 0.80 mol, it is inclined to reduce the formation rate of the cyclic polyarylene sulfide in the reaction product obtained after the reaction and increase the content of low molecular-weight compounds as the impurity content. When the amount of the arylene unit per 1 mol of the sulfur content in the reaction mixture is greater than 1.05 mol, on the other hand, it is inclined to reduce the formation rate of the cyclic polyarylene sulfide in the reaction product and increase the content of low molecular-weight compounds as the impurity content without achieving the effect of improving the formation rate of the cyclic polyarylene sulfide by performing the process 2. Accordingly, there is a need to avoid being out of the above preferable range, which increases the impurity content in the reaction product obtained after the reaction and leads directly to an increase in content of the impurities included in the resulting cyclic polyarylene sulfide after isolation and recovery of the cyclic polyarylene sulfide.

According to an exemplary embodiment of the invention, the condition of the insufficient arylene unit relative to the sulfur content, i.e., the arylene unit of not less than 0.80 mol but less than 1.00 mol per 1 mol of the sulfur content in the reaction mixture, may be preferably set in the process 1. In the prior art technique, this range causes difficulty in obtaining the objective substance and undesirably reduces the separability in solid-liquid separation for recovery of the cyclic polyarylene sulfide as described later in detail. An exemplary embodiment of the invention is, however, characterized by performing the process 2 subsequent to the process 1. The invention has been completed, based on the finding that the reaction in this range produces the objective substance without any difficulty and additionally has the advantageous effect of improving the formation rate of the cyclic polyarylene sulfide. The above condition of the insufficient arylene unit relative to the sulfur content also provides the high separability in solid-liquid separation for recovery of the cyclic polyarylene sulfide from the reaction product described later. This is also characteristic of an exemplary embodiment of the invention. According to an exemplary embodiment of the invention, setting the arylene unit per 1 mol of the sulfur content in the reaction mixture to the above preferable range in the process 1 is the preferable process, since it has the advantageous effect of further improving the formation rate of the cyclic polyarylene sulfide.

In the process 1 according to an exemplary embodiment of the invention, the linear polyarylene sulfide (d) may be included as the raw material component in the reaction mixture as described above. In this case, the content of the linear polyarylene sulfide (d) in the reaction mixture is not specifically limited as long as the raw material composition in the reaction mixture is in the range described above. It is, however, preferable that the amount of the sulfur content derived from the linear polyarylene sulfide (d) is more than half of the total amount of the sulfur content derived from the linear polyarylene sulfide and the sulfur content derived from the sulfidizing agent (b), i.e., the overall amount of the entire sulfur content in the reaction mixture. In other words, the lower limit of the amount of the sulfur content derived from the linear polyarylene sulfide relative to 1 mol of the entire sulfur content in the reaction mixture is preferably 0.5 mol, is more preferably 0.6 mol and is furthermore preferably 0.7 mol. The upper limit is preferably 0.99 mol, is more preferably 0.95 mol and is furthermore preferably 0.90 mol. Setting the content of the linear polyarylene sulfide to the above preferable range is inclined to increase the formation rate of the cyclic polyarylene sulfide relative to the used sulfidizing agent (a) in the process 2 performed subsequent to the process 1 as described later. It is economically efficient to use the linear polyarylene sulfide produced as the byproduct by the method according to an exemplary embodiment of the invention for the linear polyarylene sulfide (d).

The process 1 performs the reaction under heating of the reaction mixture of the above composition. The temperature of this reaction is preferably the temperature over the reflux temperature of the reaction mixture under ordinary pressure. This preferable temperature is varied depending on the types and the amounts of the sulfidizing agent, the dihalogenated aromatic compound and the organic polar solvent used for the reaction and is thus not unequivocally specified. The temperature is, however, generally 120° C. or higher, is preferably 180° C. or higher, is more preferably 220° C. or higher and is furthermore preferably 225° C. The temperature is also generally 350° C. or lower, is preferably 320° C. or lower, is more preferably 310° C. or lower and is furthermore preferably 300° C. or lower. In this preferable temperature range, it is inclined to allow for quick substantial reaction consumption of the sulfidizing agent (a) and the dihalogenated aromatic compound (b) to produce the cyclic PAS and the linear PAS, and it is also inclined to make the reaction proceed in a short time. The ordinary pressure herein indicates the pressure close to the standard atmosphere condition, and the standard atmosphere condition indicates the atmospheric pressure condition close to 101 kPa as the absolute pressure at the temperature around 25° C. The reflux temperature indicates the temperature in the state that the liquid component of the reaction mixture repeats boiling and condensation. According to an exemplary embodiment of the invention, it is preferable to heat the reaction mixture at the temperature over the reflux temperature under ordinary pressure as described above. As the method of heating the reaction mixture in this state may be employed, for example, a method of reacting the reaction mixture under the pressure over the ordinary pressure or a method of heating the reaction mixture in a sealed vessel. The reaction may be any of a one-stage reaction proceeding at a constant temperature, a multistage reaction proceeding with increasing the temperature in stages and a reaction proceeding with varying the temperature continuously.

The reaction time in the process 1 depends on the types and the amounts of the raw materials used and the reaction temperature and is thus not unequivocally specified. The reaction time is, however, preferably equal to or more than 0.1 hours and is more preferably equal to or more than 0.5 hours. The process 2 is performed subsequent to the process 1 as described later. It is preferable to perform the process 2 after sufficient reaction consumption of the sulfidizing agent and the dihalogenated aromatic compound in the reaction mixture in the process 1. The above preferable reaction time is inclined to ensure sufficient reaction consumption of these raw material components. There is, on the other hand, no specific upper limit of the reaction time. The reaction sufficiently proceeds in 40 hours, preferably in 10 hours and more preferably in 6 hours.

The pressure in the process 1 is not specifically limited. The pressure is varied depending on, for example, the raw materials constituting the reaction mixture, the composition of the reaction mixture and the reaction temperature and is thus not unequivocally specified. The lower limit of the pressure is preferably not lower than 0.05 MPa as the gauge pressure and is more preferably not lower than 0.3 MPa. At the preferable reaction temperature according to an exemplary embodiment of the invention, there is a pressure increase caused by the self pressure of the reactant. The lower limit of the pressure at such reaction temperature is preferably not lower than 0.25 MPa as the gauge pressure and is more preferably not lower than 0.3 MPa. The upper limit of the pressure is preferably not higher than 10 MPa and is more preferably not higher than 5 MPa. This preferable pressure range is inclined to reduce the time required for the contact reaction of the linear polyarylene sulfide, the sulfidizing agent and the dihalogenated aromatic compound. A preferable method employed to control the pressure during heating of the reaction mixture to the above preferable pressure range increases the pressure in the reaction system with an inert gas as described later, at any arbitrary stage, for example, prior to start of the reaction or during reaction, but preferably prior to start of the reaction. The gauge pressure herein means a relative pressure based on the atmospheric pressure and is synonymous with a pressure difference by subtraction of the atmospheric pressure from the absolute pressure.

A third component other than the above essential components which does not significantly interfere with the reaction or a third component which has the effect of accelerating the reaction may be added to the reaction mixture. The method of performing the reaction is not specifically limited, but it is preferable that the reaction is performed under stirring condition. The temperature in the process of mixing the raw materials is not specifically limited. For example, the reaction may be performed after the raw materials are mixed at the temperature around room temperature. As another example, the reaction may be performed when the raw materials are mixed in a reaction vessel having the temperature adjusted in advance to the above preferable temperature for the reaction. The reaction may be performed continuously, while the raw materials are successively added to the reaction system.

The sulfidizing agent (a), the dihalogenated aromatic compound (b), the organic polar solvent (c) and the linear polyarylene sulfide (d) used may contain water. The water content at the start of reaction, i.e., at the stage that substantial reaction consumption of the sulfidizing agent (a) and the dihalogenated aromatic compound (b) added as the reaction mixture does not proceed is preferably equal to or greater than 0.2 mol, is more preferably equal to or greater than 0.5 mol and is furthermore preferably equal to or greater than 0.6 mol per 1 mol of the sulfur content in the reaction mixture. The above water content is also preferably equal to or less than 20.0 mol, is more preferably equal to or less than 10.0 mol and is furthermore preferably equal to or less than 8.0 mol per 1 mol of the sulfur content in the reaction mixture. When the linear polyarylene sulfide, the sulfidizing agent, the organic polar solvent, the dihalogenated aromatic compound and the other components constituting the reaction mixture contain water and when the water content in the reaction mixture exceeds the above range, an operation of reducing the water content in the reaction system may be performed to control the water content to the above range prior to start of the reaction or in the course of reaction. This is inclined to enable the reaction to proceed efficiently in short time. When the water content of the reaction mixture is less than the above preferable range, on the other hand, a preferable procedure adds water to control the water content to the above range.

When the water content in the reaction system is in the above preferable range (0.2 to 20.0 mol per 1 mol of the sulfur content in the reaction mixture), it is inclined to increase the reaction efficiency of the linear polyarylene sulfide, the sulfidizing agent and the dihalogenated aromatic compound used as the raw materials and to obtain the cyclic polyarylene sulfide efficiently in a short time. The high reaction efficiency is presumed to cause the effect of relatively suppressing a side reaction competitively proceeding with the production reaction of a cyclic polyarylene sulfide, i.e., the production reaction of impurities. The reaction proceeding under the condition of the preferable water content is thus inclined to produce a high-quality cyclic polyarylene sulfide having a low impurity rate.

The reaction consumption rate of the dihalogenated aromatic compound herein is a value calculated by the following equations. The remaining amount of the dihalogenated aromatic compound is generally determined by gas chromatography.

In the case of addition of an excess molar ratio of the dihalogenated aromatic compound relative to the sulfidizing agent:

Reaction consumption rate (%)=[(fed amount of dihalogenated aromatic compound (mol)−remaining amount of dihalogenated aromatic compound (mol))/(fed amount of dihalogenated aromatic compound (mol)−excess amount of dihalogenated aromatic compound (mol))]×100

In the case of addition of an insufficient molar ratio of the dihalogenated aromatic compound relative to the sulfidizing agent:

Reaction consumption rate (%)=[(fed amount of dihalogenated aromatic compound (mol)−remaining amount of dihalogenated aromatic compound (mol))/(fed amount of dihalogenated aromatic compound (mol))]×100

(8) Manufacture of Cyclic Polyarylene Sulfide: Process 2

In the process 2 subsequent to the process 1, the reaction further proceeds after addition of the dihalogenated aromatic compound (b) to have the arylene unit of not less than 1.05 mol and not greater than 1.50 mol per 1 mol of the sulfur content in the reaction mixture to obtain a reaction product including at least a cyclic polyarylene sulfide and a linear polyarylene sulfide.

The added amount of the dihalogenated aromatic compound in the process 2 is determined to cause the total amount of the arylene unit in the reaction mixture in the process 1 and the arylene unit derived from the newly added dihalogenated aromatic compound to be the arylene unit in the range of not less than 1.05 mol and the not greater than 1.50 mol per 1 mol of the sulfur content in the reaction mixture. Herein the lower limit of the total amount of the arylene unit after addition of the dihalogenated aromatic compound is 1.05 mol and is preferably 1.06 mol per 1 mol of the sulfur content in the reaction mixture. The upper limit is 1.50 mol, is preferably 1.30 mol, is more preferably 1.20 mol, is furthermore preferably 1.15 mol, is especially preferably 1.12 mol. The reaction proceeding in the process 2 with controlling the above total amount of the arylene unit to this range is inclined to improve the formation rate of the cyclic polyarylene sulfide. This tendency is especially remarkable when the linear polyarylene sulfide is used as a raw material component. This also achieves the advantageous effects of obtaining an extremely high-quality cyclic polyarylene sulfide, as well as significantly improving the separability in solid-liquid separation for recovery of the cyclic polyarylene sulfide described later. The added amount of the dihalogenated aromatic compound less than the above range, however, does not show any distinct improvement in formation rate of the cyclic polyarylene sulfide and degrades the separability in solid-liquid separation for recovery of the cyclic polyarylene sulfide. The added amount exceeding the above range is, on the other hand, inclined to improve the formation rate of the cyclic polyarylene sulfide and show the high separability in solid-liquid separation, but increases the remaining amount of unreacted dihalogenated aromatic compound. This requires additional equipment for recovery of such residual material and complicates the operation. Another disadvantage is increased cost for recovery.

The method of adding the dihalogenated aromatic compound as described above is not specifically limited but may be a method of intermittent addition in multiple times or a method of continuous addition at a constant speed. As described in detail with regard to the process 1, it is effectively to set the amount of the arylene unit per 1 mol of the sulfur content in the reaction mixture used in the process 1 to the condition of the insufficient amount of arylene unit relative to the sulfur content, in terms of enhancing the formation rate of the cyclic polyarylene sulfide. When this condition is employed, it is preferable to add the dihalogenated aromatic compound in the process 2 by the method of intermittent addition in multiple times and/or by the method of continuous addition at a constant speed. Especially when the amount of the arylene unit per 1 mol of the sulfur content in the reaction mixture is closer to the lower limit in the above preferable range, addition of the dihalogenated aromatic compound in the process 2 by the method of intermittent addition in multiple times and/or by the method of continuous addition at a constant speed is more effective to reduce the impurity content included in the resulting cyclic polyarylene sulfide and obtain the cyclic polyarylene sulfide of the high purity. Additionally, employing such addition technique is inclined to further enhance the formation rate of the cyclic polyarylene sulfide.

In the case of intermittent addition of the dihalogenated aromatic compound in multiple times after the process 1 performed under the condition of the insufficient amount of arylene unit relative to the sulfur content, a preferable procedure first adds the dihalogenated aromatic compound to make the amount of the arylene unit per 1 mol of the sulfur content in the reaction mixture close to 1.00 mol and then further adds the dihalogenated aromatic compound to make the amount of the arylene unit per 1 mol of the sulfur content in the reaction mixture equal to a predetermined value in the process 2. This method of intermittent addition improves the formation rate of the cyclic polyarylene sulfide, while specifically reducing the production amount of impurities.

A concrete technique employed to add the dihalogenated aromatic compound in the reaction system may be, for example, a procedure of introducing a predetermined amount of the dihalogenated aromatic compound into the reaction system via a pressure-resistant vessel or a method of pressing the dihalogenated aromatic compound in the molten state or a solution of the dihalogenated aromatic compound in the organic polar solvent into the reaction system by means of a pressure pump.

It is preferable to add the dihalogenated aromatic compound after sufficient reaction consumption of the sulfidizing agent in the reaction mixture. Specifically, addition of the dihalogenated aromatic compound is after the reaction proceeding until 50% or more of the sulfidizing agent is consumed as the lower limit for the reaction, is preferably after the reaction proceeding until 60% or more of the sulfidizing agent is consumed for the reaction, is more preferably after the reaction proceeding until 70% or more of the sulfidizing agent is consumed for the reaction, is furthermore preferably after the reaction proceeding until 80% or more of the sulfidizing agent is consumed for the reaction and is especially preferably after the reaction proceeding until 90% or more of the sulfidizing agent is consumed for the reaction. Addition of the dihalogenated aromatic compound after reaction consumption of the sulfidizing agent to the above range is of significant importance to suppress production of the impurities and improve the quality and the purity of the resulting cyclic polyarylene sulfide. The reaction consumption of the sulfidizing agent less than 50% increases the impurity content in a reaction product obtained after the reaction. Such an increase in impurity content leads directly to an increase in content of the impurities included in the resulting cyclic polyarylene sulfide after isolation and recovery of the cyclic polyarylene sulfide and should thus be avoided.

In the method according to an exemplary embodiment of the invention, the reaction consumption rate of the sulfidizing agent may be calculated by quantitatively determining the amount of the sulfidizing agent remaining in the reaction mixture by ion chromatography technique using, for example, an electrical conductivity detector or an electrochemical detector. In this application, the reaction consumption rate of the sulfidizing agent is calculated as the ratio of the amount of reaction consumption of the sulfidizing agent (amount by subtracting the remaining amount of the sulfidizing agent in the reaction mixture from the fed amount of the sulfidizing agent) to the fed amount of the sulfidizing agent. As the specific evaluation method using ion chromatography technique may be employed a procedure that adds a hydrogen peroxide solution to a sample to oxidize sulfide ion included in the sample and subsequently perform analysis using an electrical conductivity detector to calculate the amount of sulfate ion produced by oxidation of the sulfide ion. The procedure quantitatively determines the remaining amount of the sulfidizing agent from the calculated amount of the sulfate ion and then calculates the above reaction consumption rate of the sulfidizing agent.

In the process 2, the reaction further proceeds after addition of the dihalogenated aromatic compound. The preferable conditions in the process 1 described in the preceding section (7) may be employed for the conditions of this reaction, such as the temperature, the pressure and the water content.

More specifically, the reaction temperature in the process 2 is preferably a temperature exceeding the reflux temperature of the reaction mixture under ordinary pressure. The temperature employed in the process 2 may be higher than the temperature employed in the process 1 and is specifically equal to or higher than 180° C., is more preferably equal to or higher than 220° C., is furthermore preferably equal to or higher than 225° C., is further preferably equal to or higher than 250° C. and is especially preferably equal to or higher than 260° C. The temperature in the process 2 is also specifically equal to or lower than 320° C., is more preferably equal to or lower than 310° C. and is furthermore preferably equal to or lower than 300° C. This preferable temperature range is inclined to reduce the impurity content under the higher temperature condition than the temperature in the process 1, as well as to make the reaction proceed in a short time.

The reaction time in the process 2 depends on the types and the amounts of the raw materials used and the reaction temperature and is thus not unequivocally specified. Since most part of the fed sulfidizing agent has been already consumed in the process 1, the shorter reaction time than the reaction time in the process 1 enables the reaction to sufficiently proceed. The lower limit of the preferable reaction time is specifically not less than 0.1 hours and is more preferably not less than 0.25 hours. As the upper limit of the preferable reaction time, the reaction sufficiently proceeds in 20 hours, preferably in 5 hours and more preferably in 3 hours.

A variety of known polymerization systems and reaction systems, such as batch system and continuous system, may be employed for the reactions in the process 1 and the process 2. The desirable atmosphere during manufacture is a non-oxidizing atmosphere, and manufacture is preferably performed under an inert gas atmosphere such as nitrogen, helium or argon. In terms of the economic efficiency and the easiness of handling, nitrogen atmosphere is especially preferable.

(9) Solid-Liquid Separation of Reaction Product: Process 3

An exemplary embodiment of the invention performs the process 1 and the process 2 described above to obtain a reaction product including at least a cyclic polyarylene sulfide and a linear polyarylene sulfide. The organic polar solvent used in the process 1 and the process 2 is generally included in the reaction product.

An exemplary embodiment of the invention preferably performs a process 3 subsequent to the above process 1 and process 2, i.e., a process of performing solid-liquid separation of the reaction product obtained as described above in a temperature range of not higher than the boiling point of the organic polar solvent under ordinary pressure, so as to obtain a filtrate including the cyclic polyarylene sulfide and the organic polar solvent. This process 3 performed for the reaction product enables the cyclic polyarylene sulfide and the linear polyarylene sulfide in the reaction product to be readily separated from each other.

The temperature of solid-liquid separation of the reaction product is preferably not higher than the boiling point of the organic polar solvent under ordinary pressure. The specific temperature depends on the type of the organic polar solvent but is, for example, equal to or higher than 10° C., is more preferably equal to or higher than 15° C. and is furthermore preferably equal to or higher than 20° C. The temperature is also, for example, equal to or lower than 200° C., is more preferably equal to or lower than 150° C. and is furthermore preferably equal to or lower than 120° C. The above temperature range is inclined to increase the solubility of the cyclic polyarylene sulfide in the organic polar solvent but decrease the solubility of the components other than the cyclic polyarylene sulfide included in the reaction product, especially, the linear polyarylene sulfide inevitably included in the reaction product, in the organic polar solvent. Solid-liquid separation in this temperature range is thus effective to obtain a high-quality cyclic polyarylene sulfide with high accuracy as the filtrate component.

The method of performing solid-liquid separation is not specifically limited but may be, for example, filtration using a filter, such as pressure filtration or suction filtration, separation based on the specific gravity difference between the solid content and the solution, such as centrifugal separation or precipitation separation, or any combination of these techniques. The technique of pressure filtration or suction filtration using a filter may be preferably employed as the simpler method. The filter used for filtration operation may be any filter material that is stable under the conditions of solid-liquid separation, for example, a general filter material such as wire mesh filter, sintered plate, filter cloth or filter paper.

The pore size of the filter is adjustable over a wide range, depending on the viscosity of a slurry subjected to the solid-liquid separation, the pressure, the temperature and the particle size of the solid component in the reaction product. It is especially effective to select the pore size of the filter, such as the mesh size or the micro-pore size, depending on the particle size of the linear polyarylene sulfide recovered as the solid content from the reaction product by this solid-liquid separation, i.e., the particle size of the solid component present in the reaction product subjected to solid-liquid separation. The mean particle size (median size) of the solid component in the reaction product subjected to solid-liquid separation is varied over a wide range, depending on the composition, the temperature and the concentration of the reaction product. To the inventors' knowledge, the mean particle size is inclined to be 1 to 200 µm. The preferable mean pore size of the filter is, for example, equal to or greater than 0.1 µm, is preferably equal to or greater than 0.25 µm and is more preferably equal to or greater than 0.5 µm. The mean pore size is, for example, equal to or less than 100 is preferably equal to or less than 20 µm and is more preferably equal to or less than 15 µm. Using the filter material having the mean pore size in the above range is inclined to reduce the amount of the linear polyarylene sulfide transmitted through the filter material and obtain the high purity cyclic polyarylene sulfide.

The atmosphere of solid-liquid separation is not specifically limited. In the case that the cyclic polyarylene sulfide, the organic polar solvent and the linear PAS are deteriorated by oxidation under certain conditions of the exposure time and temperature, it is preferable to perform solid-liquid separation under a non-oxidizing atmosphere. The non-oxidizing atmosphere herein indicates an atmosphere having the oxygen concentration of not higher than 5% by volume, preferably having the oxygen concentration of not higher than 2% by volume and more preferably having no substantial content of oxygen in the gas phase and specifically an inert gas atmosphere such as nitrogen, helium or argon. Among them, it is preferable to perform solid-liquid separation under nitrogen atmosphere, in terms of the economic efficiency and the easiness of handling.

The type of the filter used for solid-liquid separation may be, for example, a sieve, a vibrating screen, a centrifugal separator, a precipitation separator, a pressure filter or a suction filter, although these are not restrictive. In terms of performing solid-liquid separation under the non-oxidizing atmosphere which is the favorable atmosphere for solid-liquid separation as described above, it is preferable to select a filter having a mechanism that readily maintains the non-oxidizing atmosphere during solid-liquid separation. Available examples of such filter include a filter that enables filtration operation to be performed in a sealed state after substitution of the atmosphere in the filter with an inert gas and a filter equipped with a mechanism of performing filtration operation with flowing an inert gas. Among the filters mentioned above, the centrifugal separator, the precipitation separator and the pressure filter are preferable, since this mechanism is readily attachable to these filters. The pressure filter is especially preferable, in terms of the simple mechanism and the excellent economic efficiency.

The pressure during solid-liquid separation is not specifically limited, but solid-liquid separation may be performed under pressurized condition using the pressure filter mentioned above, in order to complete solid-liquid separation in a shorter time. More specifically, the pressure range is preferably equal to or less than 2.0 MPa as the gauge pressure, is more preferably equal to or less than 1.0 MPa, is furthermore preferably equal to or less than 0.8 MPa and is especially preferably equal to or less than 0.5 MPa. In general, equipment used for solid-liquid separation needs to have the higher pressure resistance with an increase in pressure. This leads to a need for the high sealing properties at the respective parts constituting the equipment and thus naturally increases the cost of equipment. The above preferable pressure range, however, allows for the use of a commonly available solid-liquid separator.

Performing the process 1 and the process 2 which are characteristic of the production method of the cyclic polyarylene sulfide according to an exemplary embodiment of the invention achieves solid-liquid separation of the resulting reaction product at extremely high efficiency. This advantageous effect of excellent solid-liquid separability is also a remarkable characteristic of an exemplary embodiment of the invention. The solid-liquid separability herein may be evaluated by the time required for solid-liquid separation of a fixed amount of the reaction product. A concrete evaluation procedure places a filter material (filter) of predetermined specifications (pore size and material) and a fixed area in, for example, a sealable pressure filtration device, filters a predetermined amount of the reaction product through the filter material and measures the time required to obtain a specified amount of filtrate under fixed conditions (e.g., temperature and pressure). This allows for comparison and evaluation by the filtration speed in the unit of weight/(area·time). More specifically, this allows for evaluation by measuring the time required to obtain a specified amount of filtrate when the reaction product is filtered through a PTFE membrane filter having the mean pore size of 10 μm under the conditions of 100° C. and 0.1 MPa. The reaction product obtained by the conventional production method of the cyclic polyarylene sulfide has the problems of extremely poor filtration performance and low filtration speed in such evaluation of the solid-liquid separability. This is attributed to the fact that the prior art technique does not perform the process 1 and the process 2, which are the essential processed according to an exemplary embodiment of the invention. An exemplary embodiment of the invention is inclined to achieve the significantly high filtration speed of not less than 50 kg/(m²·hr). Selection of the preferable numerical ranges for the various factors described above with respect to the process 1 and the process 2 of manufacture of the cyclic polyarylene sulfide achieves the remarkably high filtration speed of not less than 100 kg/(m²·hr) and even the extremely high filtration speed of 150 kg/(m²·hr).

An operation of distilling out part of the organic polar solvent included in the reaction product to reduce the volume of the organic polar solvent in the reaction product may additionally be performed, prior to solid-liquid separation of the reaction product. This decreases the amount of the reaction product subjected to solid-liquid separation and is thereby inclined to reduce the time required for solid-liquid separation.

The method employed to distill out the organic polar solvent may be any technique that separates the organic polar solvent from the reaction product and reduces the volume of the organic polar solvent contained in the reaction product. Preferable techniques include a method of distilling the organic polar solvent under reduced pressure or under pressure and a method of flushing out the solvent for removal. Especially preferable is the method of distilling the organic polar solvent under reduced pressure or under pressure. An inert gas such as nitrogen, helium or argon may be used as the carrier gas in the process of distilling the organic polar solvent under reduced pressure or under pressure.

The temperature for distilling out the organic polar solvent is varied depending on the type of the organic polar solvent and the composition of the reaction product and is thus not unequivocally specified. The temperature is, however, preferably equal to or higher than 180° C. and is more preferably equal to or higher than 200° C. The temperature is also preferably equal to or lower than 300° C., is more preferably equal to or lower than 280° C. and is furthermore preferably equal to or lower than 250° C.

This solid-liquid separation enables most part of the cyclic polyarylene sulfide included in the reaction product to be separated as the filtrate component and more specifically enables preferably not less than 80%, more preferably not less than 90% and furthermore preferably not less than 95% of the cyclic polyarylene sulfide to be recovered as the filtrate component. When part of the cyclic polyarylene sulfide remains in the linear polyarylene sulfide separated as the solid content by solid-liquid separation, the solid content may be washed with a new organic polar solvent, in order to reduce the remaining amount of the cyclic polyarylene sulfide in the solid content. The solvent used for this purpose may be any solvent that is capable of dissolving the cyclic polyarylene sulfide, but is preferably the same solvent as the organic polar solvent used in the process 1 or the process 2 described above.

(10) Separation of Cyclic Polyarylene Sulfide

According to an exemplary embodiment of the invention, the cyclic polyarylene sulfide may be recovered by separating the cyclic polyarylene sulfide from the filtrate component obtained by solid-liquid separation described above. The method of recovery is not specifically limited but may be, for example, a method of removing some part or most part of the organic polar solvent in the filtrate by distillation or other operation as appropriate and subsequently exposing the filtrate, under heating as appropriate, to a solvent which has low solubility for the cyclic polyarylene sulfide and has the characteristic of being miscible with the organic polar solvent, so as to recover the cyclic polyarylene sulfide in the form of a solid. The solvent having such characteristics is generally a solvent having relatively high polarity. The preferable solvent differs depending on the type of the organic polar solvent in the filtrate and the type of a byproduct included in the filtrate and is thus not specifically limited. Available examples of the solvent include: water; alcohols such as methanol, ethanol, propanol, isopropyl alcohol, butanol and hexanol; ketones such as acetone; and acetates such as ethyl acetate and butyl acetate. In terms of the availability and the economic efficiency, water, methanol and acetone are preferable, and water is especially preferable. In the above recovery operation, it is preferable to separate and recover 50% by weight or more of the cyclic polyarylene sulfide included in the filtrate as the solid content by adding water to the filtrate.

With regard to the weight fraction of the cyclic polyarylene sulfide in the filtrate, the higher content rate generally results in the higher yield of the cyclic polyarylene sulfide obtained after the recovery operation and enables the cyclic polyarylene sulfide to be recovered with the higher efficiency. From this aspect, the content rate of the cyclic polyarylene sulfide in the filtrate is preferably equal to or more than 0.5% by weight, is more preferably equal to or more than 1% by weight, is furthermore preferably equal to or more than 2% by weight and is especially preferably equal to or more than 5% by weight. There is, on the other hand, no specific upper limit of the content rate of the cyclic polyarylene sulfide in the filtrate, but the excessively high content rate is inclined to produce an insoluble component, which may cause some inconvenience in the recovery operation. The inconvenience in the recovery operation is, for example, non-uniform properties of the filtrate (which may be a slurry including the solid content) before the preferable operation of adding water, which locally changes the composition and degrades the quality of the recovered product. The tendency of causing such an inconvenience depends on the properties of the organic polar solvent and the conditions during preparation of the reaction mixture. The upper limit of the content rate of the cyclic polyarylene sulfide in the filtrate is thus not specified, but is generally equal to or less than 20% by weight, is preferably equal to or less than 15% by weight and is more preferably equal to or less than 10% by weight.

The filtrate may be heated, in order to avoid any inconvenience in the recovery operation described above and further increase the content rate of the cyclic polyarylene sulfide in the filtrate. This heating temperature is varied depending on the properties of the organic polar solvent used and is thus not unequivocally specified. The heating temperature is, however, preferably equal to or higher than 50° C., is more preferably equal to or higher than 70° C. and is furthermore specifically equal to or higher than 90° C. The upper limit of the heating temperature is, on the other hand, preferably not higher than the boiling point of the used organic polar solvent under ordinary pressure. This temperature range is preferably inclined to ensure the stable recovery operation while maintaining the high content of the cyclic polyarylene sulfide in the filtrate. An additional operation such as stirring or shaking may be performed during preparation of this mixture. Such operation is desirable in terms of maintaining the filtrate in the more homogeneous condition.

In this recovery method, it is preferable to add water to the filtrate, in order to precipitate and recover, as the solid content, the cyclic polyarylene sulfide dissolved in the organic polar solvent. The method of adding water to the filtrate is not specifically limited, but a method of producing a coarse solid content by addition of water should be avoided. A preferable procedure adds water dropwise to the filtrate with stirring. The temperature in the operation of water addition is not specifically limited, but the lower temperature is more inclined to produce a coarse solid content by addition of water. In terms of avoiding such an inconvenience in operation and maintaining the homogeneity of the mixture, the temperature is preferably equal to or higher than 50° C., is more preferably equal to or higher than 70° C. and is furthermore specifically equal to or higher than 90° C. The upper limit of the temperature in the operation of water addition is, on the other hand, preferably not higher than the boiling point of the used organic polar solvent under ordinary pressure. The operation of water addition in this preferable temperature range is inclined to enable the recovery operation to be performed by the simpler method in terms of the operability and the equipment.

The method of recovering the cyclic PAS by addition of water to the filtrate including the cyclic PAS described above enables the cyclic PAS to be obtained with the higher efficiency by using even a less volume of the solvent, compared with the reprecipitation technique conventionally employed as the method of recovering the cyclic PAS from the filtrate including the cyclic PAS. The above method thus significantly reduces the weight of water added to the filtrate including the cyclic PAS and the organic solvent. More specifically, the weight of water to be added to the filtrate may be set equal to or less than 50% by weight as the water content relative to the total volume of the organic polar solvent and water after addition of water, may be set equal to or less than 40% by weight as the more preferable condition and may be set equal to or less than 35% by weight as the furthermore preferable condition. There is, on the other hand, no specific lower limit of the weight of water to be added. In order to recover the cyclic PAS as the solid content with the high efficiency, however, the lower limit is preferably equal to or more than 5% by weight and is more preferably equal to or more than 10% by weight. The preferable method is capable of recovering 50% by weight or more of the cyclic PAS included in the filtrate as the solid content. The preferable range of the used amount of water described above is inclined to recover 80% by weight or more of the cyclic PAS as the solid content and recover more preferably 90% by weight or more, furthermore preferably 95% by weight or more and especially preferably 98% by weight or more of the cyclic PAS as the solid content.

The amount of water in the filtrate herein indicates the sum of the amount of water included in the reaction mixture before solid-liquid separation and the amount of water added to the filtrate. There is a need to determine the amount of water added to the filtrate by taking into account the amount of water included in the reaction mixture.

The filtrate mixture which is obtained by the above series of operations and includes the cyclic PAS, the organic polar solvent and water is inclined to have, as the solid content, 50% by weight or more of the cyclic PAS which is included in the filtrate. The cyclic PAS may thus be recovered in the form of a solid by using any known solid-liquid separation technique. The available solid-liquid separation technique is, for example, separation by filtration, centrifugal separation or decantation. In order to further enhance the recovery rate of the cyclic PAS, solid-liquid separation is performed after the temperature of the filtrate mixture is controlled to be preferably lower than 50° C., preferably not higher than 40° C. and more preferably not higher than 30° C. Recovery of the cyclic PAS after such temperature control to the preferable temperature has the advantageous effects of not only enhancing the recovery rate of the cyclic PAS but enabling the cyclic PAS to be recovered by the simpler equipment. There is no specific lower limit of the temperature of the filtrate mixture. It is, however, desirable to avoid such temperature decreasing conditions as to excessively increase the viscosity of the filtrate mixture and as to solidify the filtrate mixture. In general, the most desirable temperature condition is around ordinary temperature.

Such solid-liquid separation is inclined to isolate and recover, as the solid content, 50% by weight or more of the cyclic PAS which is present in the filtrate mixture. When the cyclic PAS in the solid form separated by the above procedure includes the liquid component of the filtrate mixture (mother liquid), the amount of the mother liquid may be reduced by washing the cyclic PAS in the solid form with a variety of solvents. The variety of solvents used for washing the cyclic PAS in the solid-liquid form are preferably solvents which have low solubility for the cyclic PAS. Available examples of such solvent include: water; alcohols such as methanol, ethanol, propanol, isopropyl alcohol, butanol and hexanol; ketones such as acetone; and acetates such as ethyl acetate and butyl acetate. In terms of the availability and the economic efficiency, water, methanol and acetone are preferable, and water is especially preferable. Additional washing using such a solvent has the advantageous effects of not only reducing the amount of the mother liquid contained in the cyclic PAS in the solid form but reducing the impurities soluble in the solvent included in the cyclic PAS. The technique for such washing may be a method of performing solid-liquid separation by adding a solvent on a separation filter, on which the solid cake deposits or a method of adding a solvent to the solid cake with stirring to prepare a slurry and subsequently performing solid-liquid separation again. Additionally, a general drying operation may be preformed for the cyclic PAS in the wet state containing a liquid component, for example, containing the mother liquid described above or containing the solvent component used for the washing operation. This removes the liquid component and provides the cyclic PAS in the dry state.

The atmosphere during the recovery operation of the cyclic PAS is preferably a non-oxidizing atmosphere. This is inclined to suppress not only undesirable side reactions during recovery of the cyclic PAS, for example, cross-linking reaction, degradation reaction and oxidation reaction of the cyclic PAS but undesirable side reactions such as oxidation degradation of the organic polar solvent used for the recovery operation. The non-oxidizing atmosphere herein indicates an atmosphere having the oxygen concentration of not higher than 5% by volume, preferably having the oxygen concentration of not higher than 2% by volume and more preferably having no substantial content of oxygen in the gas phase, to which the variety of components as the object of the recovery operation are exposed, and specifically an inert gas atmosphere such as nitrogen, helium or argon. Among them, nitrogen atmosphere is especially preferable in terms of the economic efficiency and the easiness of handling.

(11) Properties of Cyclic PAS Recovered According to Embodiment of Invention

The cyclic PAS thus obtained is highly pure cyclic PAS including generally 50% by weight or more, preferably 70% by weight or more and more preferably 80% by weight or more of the cyclic PAS and has different properties from those of the generally obtained linear PAS to have a great deal of potential in industry. The cyclic PAS manufactured by the production method according to an exemplary embodiment of the invention is unlikely to have a single repeating number m in the formula (Q) given above but is characteristically likely to have different repeating numbers m=4 to 50 in the above formula (Q). The range of m is preferably 4 to 30 and is more preferably 4 to 25. The repeating number m in this range is inclined to melt the PAS at lower temperatures in the case of mixing the cyclic PAS with a variety of resins described later. This is also inclined to accelerate the polymerization reaction in the process of conversion from a prepolymer including the cyclic PAS to a polymer of high degree of polymerization and obtain a high molecular-weight polymer. This reason is not yet elucidated but may be attributed to that the cyclic PAS having m in this range has high bond strain due to ring molecules, which accelerates the ring-opening reaction during polymerization. The cyclic PAS having a single repeating number m is obtained as a single crystal and has an extremely high melting temperature. The cyclic PAS according to an exemplary embodiment of the invention is, on the other hand, characteristically likely to be obtained as a mixture having different repeating numbers m and thereby have a low melting temperature. This leads to the advantageous characteristic of decreasing the heating temperature in application of the cyclic PAS in the melted state.

The cyclic PAS according to an exemplary embodiment of the invention also has the excellent characteristic of an extremely low content of a low molecular-weight compound (hereinafter may be referred to as low molecular-weight PAS) having different structure from that of the cyclic PAS consisting of the arylene sulfide unit. Such low molecular-weight compound has different properties from those of the cyclic PAS and those of the linear PAS having a sufficiently high molecular weight. For example, this low molecular-weight compound has poor heat resistance and may contribute to increase outgassing under heating, for example, during molding process. The low molecular-weight compound also has adverse effects, for example, by acting as a component interfering with polymerization when the cyclic PAS is used as the prepolymer of a high molecular-weight polymer described later. The production method of the cyclic PAS according to an exemplary embodiment of the invention includes the process 1 and the process 2 and accordingly achieves the advantageous characteristic of providing the high-quality PAS with significant reduction of the low molecular-weight PAS.

The content of the low molecular-weight PASes contained in the cyclic PAS as the impurities may be calculated from peak areas in component separation by high-performance liquid chromatography using a UV detector and an ODS column. The weight fraction of the low molecular-weight PASes in the isolated solid of the cyclic PAS including the low molecular-weight PASes may be calculated by this technique. As another example, the content rate of the low molecular-weight PASes may be calculated as the peak area ratio or more specifically the ratio of the total area of peaks attributed to the low molecular-weight PASes (corresponding to peaks other than the peaks attributed to the cyclic PAS) to the total area of detected peaks, based on the peak areas detected by high-performance liquid chromatography.

An exemplary embodiment of the invention provides the high-quality cyclic PAS having an extremely low content of the low molecular-weight PAS as described above. The preferable production method according to an exemplary embodiment of the invention provides the extremely high-quality cyclic PAS having the weight fraction of the low molecular-weight PAS by the above evaluation technique of 7% by weight or less, preferably 5% by weight or less and more preferably 3% by weight or less. In evaluation by the peak area ratio of the low molecular-weight compound, when the ratio of peaks attributed to substances other than cyclic polyphenylene sulfide is defined as the impurity rate, the preferable method according to an exemplary embodiment of the invention provides the cyclic PAS having the impurity rate of 9% by weight or less, preferably 6% by weight or less and more preferably 4% by weight or less.

(12) Resin Composition Including Cyclic PAS Recovered According to Embodiment of Invention The cyclic PAS obtained according to an exemplary embodiment of the invention may be used as a composition with a variety of resins. The resin composition including this cyclic PAS is inclined to have excellent flowability and excellent thermal stability during melt processing. Such characteristic, especially the improved flowability, leads to the excellent melt processability even at low heating temperature during melt processing of the resin composition and thus advantageously improves the melt processability in manufacture of injection molded products and extrusion molded products such as fibers and films. The reason of this improvement in characteristic by mixing the cyclic PAS is not elucidated but may be attributed to the structural specificity of the cyclic PAS, i.e., the compact geometry due to the ring structure compared with the general linear compound. This structural specificity makes the cyclic PAS likely to have little tangles with a variety of resins used as the matrix, act as a plasticizer to a variety of resins and suppress tangles between the matrix resin.

The mixing amount of the cyclic PAS mixed with a variety resins is not specifically limited, but significant improvement of the characteristic is achievable by mixing 0.1 parts by weight or more or preferably 0.5 parts by weight or more of the cyclic PAS according to an exemplary embodiment of the invention relative to 100 parts by weight of the variety of resins. Significant improvement of the characteristic is also achievable by mixing 50 parts by weight or less, preferably 20 parts by weight or less or more preferably 10 parts by weight or less of the cyclic PAS.

Additionally, fibrous and/or non-fibrous fillers may be additionally mixed in the above resin composition as appropriate. The mixing amount of the filler is, for example, 0.5 parts by weight or more and is preferably 1 part by weight or more relative to 100 parts by weight of the above variety of resins. The mixing amount of the filler is also, for example, 400 parts by weight or less, is preferably 300 parts by weight or less, is more preferably 200 parts by weight or less and is furthermore preferably 100 parts by weight or less. Controlling the mixing amount of the filler to this range is inclined to improve the mechanical strength of the resin composition while maintaining the excellent flowability. The available type of the filler may be any of fibrous, plate-like, powdery and granular fillers. Preferable specific examples of the filler include glass fibers, talc, wollastonite, montmorillonite and layered silicates such as synthetic mica. Especially preferable are glass fibers. The available type of the glass fiber is not specifically limited but may be any glass fiber generally used for reinforcement of resin. The glass fiber used may be selected, for example, among long fiber-type and short-fiber type chopped strands and milled fibers. Two or more of the above fillers may be used in combination. The above filler used according to the embodiment of the invention may be used after surface treatment with a known coupling agent (for example, silane coupling agent, titanate coupling agent) or another surface treatment agent. The glass fibers may be coated with or sized with a thermoplastic resin such as ethylene-vinyl acetate copolymer or a thermosetting resin such as epoxy resin.

In order to maintain thermal stability of the resin composition, one or more heat resistant material selected among phenolic compounds and phosphorous compounds may be contained in the resin composition. In terms of the effect of improving the heat resistance, the mixing amount of the heat resistant material is equal to or more than 0.01 parts by weight and is preferably equal to or more than 0.02 parts by weight relative to 100 parts by weight of the above variety of resins. In terms of the gas component generated during molding, the mixing amount of the heat resistant material is equal to or less than 5 parts by weight and is preferably equal to or less than 1 part by weight relative to 100 parts by weight of the above variety of resins. Combined use of the phenolic compound with the phosphorus compound is especially preferable, since it has significant effects of maintaining heat resistance, thermal stability and flowability.

The following compound may further be mixed in the above resin composition: coupling agents such as organotitanate compounds and organoborane compounds; plasticizers such as poly(alkylene oxide) oligomer compounds, thioether compounds, ester compounds and organophosphorus compounds; crystal nucleating agents such as talc, kaolin, organophosphorus compounds and poly(ether ether ketone)s; metal soaps such as montanic acid waxes, lithium stearate and aluminum stearate; mold release agents such as polycondensation products of ethylene diamine/stearic acid/sebacic acid and silicone compounds; color protection agents such as hypophosphites; and other general additives including lubricants, ultraviolet protection agents, coloring agents, flame retardants and foaming agents. Addition of any of the above compounds by the amount of less than 20 parts by weight, preferably the amount of not more than 10 parts by weight or more preferably the amount of not more than 1 part by weight relative to 100 parts by weight of the above variety of resins is inclined to have the beneficial effects.

The method of manufacturing the resin composition including the cyclic PAS described above is not specifically limited. For example, an applicable method may premix the cyclic PAS with the variety of resins and optionally the other fillers and the variety of additives and melt-kneads the mixture at temperatures of not lower than the melting points of the variety of resins and the cyclic PAS by a generally known melt mixing machine, such as a single-screw extruder, a twin-screw extruder, a Banbury mixer, a kneader, or a mixing roll. Another applicable method may premix the materials of the resin composition in a solution and remove a solvent. In applications that the cyclic PAS used is a simple cyclic PAS, i.e., a cyclic PAS having a single repeating number m in the above formula (Q) or is a mixture of cyclic PASes of different repeating numbers m having high crystallinity and a high melting point, an applicable method may dissolve the cyclic PAS in a solvent that is capable of dissolving the cyclic PAS, feed the cyclic PAS-dissolved solution to a melt mixing machine and remove the solvent during melt-kneading. In such applications, another applicable method may melt the cyclic PAS at the temperature of not lower than its melting point, rapidly cool the melt cyclic PAS to suppress crystallization and feed the cyclic PAS in amorphous form to a melt mixing machine. In such applications, yet another applicable method may set a pre-melter at the temperature of not lower than the melting point of the cyclic PAS, melt only the cyclic PAS in the pre-melter and feed the melt cyclic PAS to a melt mixing machine.

There is no specific limitation with respect to the variety of resins mixed with the cyclic PAS. The invention is applicable to both crystalline resins and amorphous resins, as well as to both thermoplastic resins and thermosetting resins.

Specific examples of the crystalline resin include polyolefin resins such as polyethylene resins, polypropylene resins and syndiotactic polystyrene, polyvinyl alcohol resins, polyvinylidene chloride resins, polyester resins, polyamide resins, polyacetal resins, polyphenylene sulfide resins, poly(ether ether ketone) resins, polyether ketone resins, polyketone resins, polyimide resins and their copolymers. One of such resins or a combination of two or more of such resins may be used. Among them, in terms of the heat resistance, the moldability, the flowability and the mechanical properties, polyphenylene sulfide resins, polyamide resins and polyester resins are preferable. In terms of the transparency of the resulting molded product, polyester resins are preferable. Using the crystalline resin as the variety of resins is inclined to improve the crystallization characteristics, in addition to improvement of the flowability described above. It is especially preferable to use the polyphenylene sulfide resin as the variety of resins. This is inclined to achieve improvement of the crystallinity along with improvement of the flowability and is additionally inclined to significantly suppress the appearance of burrs during injection molding as the result of such improvements.

The amorphous resin is not specifically limited but may be any amorphous resin that is melt-moldable. In terms of the heat resistance, however, the amorphous resin used has the glass transition temperature of preferably not lower than 50° C., more preferably not lower than 60° C., furthermore preferably not lower than 70° C. or especially preferably not lower than 80° C. The upper limit of the glass transition temperature is not specifically limited, but in terms of, for example, the moldability, the upper limit is preferably not higher than 300° C. and is more preferably not higher than 280° C. According to an exemplary embodiment of the invention, the glass transition temperature of the amorphous resin indicates a glass transition temperature (Tg) observed by differential calorimetry that heats the amorphous resin at a temperature rise condition of 20° C./minute from 30° C. to an expected glass transition temperature or higher, keeps the amorphous resin at the raised temperature for 1 minute, subsequently cools the amorphous resin to 0° C. at a temperature decrease condition of 20° C./minute, keeps the amorphous resin at the decreased temperature for 1 minute and then makes a measurement at a temperature re-rise condition of 20° C./minute. A specific example of such amorphous resin may be at least one selected among amorphous nylon resins, polycarbonate (PC) resins, polyarylate resins, ABS resins, poly(meth)acrylate resins, poly(meth)acrylate copolymers, polysulfone resins and polyether sulfone resins. One of such resins or a combination of two or more of such resins may be used. Among these amorphous resins, preferably used are polycarbonate (PC) resins having especially high transparency, transparent ABS resins included in ABS resins, polyarylate resins, poly(meth)acrylate resins, poly(meth)acrylate copolymers and polyether sulfone resins. Using the amorphous resin having excellent transparency as the variety of resins has the advantageous characteristic of maintaining the high transparency, in addition to improvement of the flowability during melt processing described above. When the high transparency is desired for the amorphous resin composition, it is preferable to use a mixture of cyclic PASes having different repeating numbers m in the above formula (Q) as the cyclic PAS. A simple cyclic PAS, i.e., a cyclic PAS having a single repeating number m in the above formula (Q), used as the cyclic PAS is inclined to be only insufficiently melted and dispersed during melt-kneading with the amorphous resin, thereby producing aggregates in the resin and decreasing the transparency, due to the high melting point of such simple cyclic PAS. A mixture of cyclic PASes having different repeating numbers m in the above formula (Q) is, on the other hand, inclined to have the low melting point as described above, which is advantageous for improving the homogeneity during melt-kneading. The cyclic PAS manufactured by the production method according to an exemplary embodiment of the invention is unlikely to have a single repeating number m in the above formula (Q) but is characteristically likely to have different repeating numbers m=4 to 50 in the above formula (Q). This is especially advantageous when the amorphous resin composition obtained is desired to have high transparency.

The resin composition obtained by mixing the cyclic PAS with the variety of resins as described above may be molded by any of generally known techniques, for example, injection molding, extrusion molding, blow molding, press molding or spinning and processed to and used as a variety of molded products. Available examples of the molded products include injection molded products, extrusion molded products, blow molded products, films, sheets and fibers. The variety of products thus obtained may be used in a variety of applications including automobile parts, electric and electronic parts, architectural components, various vessels and containers, daily necessities, household goods and sanitary articles. The above resin composition and its molded products are recyclable. For example, a resin composition obtained by pulverizing the above resin composition and its molded products preferably to the powder level and blending additives as appropriate with the powder may be used similarly to the above resin composition and may be processed to a molded product.

(13) Conversion of Cyclic PAS to Polymer of High Degree of Polymerization

The cyclic PAS recovered according to an exemplary embodiment of the invention has the excellent characteristics as described in the preceding section (11) and may thus be preferably used as a prepolymer for production of a PAS polymer, i.e., a polymer of high degree of polymerization. The prepolymer herein may be the cyclic PAS alone obtained by the recovery method of the cyclic PAS according to an exemplary embodiment of the invention or may be the cyclic PAS including certain amounts of other components. When components other than the cyclic PAS are included, it is especially preferable that such components are PASes, for example, linear PAS and PAS of branch structure. A polyarylene sulfide prepolymer includes at least the cyclic PAS according to an exemplary embodiment of the invention and is enabled to be converted to a polymer of high degree of polymerization by a method described below. This may be hereinafter referred to as PAS prepolymer.

Conversion of the cyclic PAS to a polymer of high degree of polymerization may be performed under conditions that produce the polymer of high degree of polymerization from the cyclic PAS as the raw material. For example, a preferable method may heat the PAS prepolymer including the cyclic PAS manufactured by the production method of the cyclic PAS according to an exemplary embodiment of the invention to convert the PAS prepolymer to the polymer of high degree of polymerization. The temperature of such heating is preferably the temperature of melting the above PAS prepolymer. There is no specific limitation of this temperature condition. The heating temperature of lower than the melting temperature of the PAS prepolymer is inclined to increase the time required for obtaining the high molecular-weight PAS. The melting temperature of the PAS prepolymer depends on the composition and the molecular weight of the PAS prepolymer and the environment during heating and is thus not unequivocally specified. The melting point may, however, be obtained, for example, by analyzing the PAS prepolymer with a differential scanning calorimeter. The excessively high heating temperature is inclined to cause undesirable side reactions, such as cross-linking reaction and degradation reaction of the PAS prepolymer, of the resulting PAS produced by heating and between the resulting PAS produced by heating and the PAS prepolymer, which may result in degrading the characteristics of the resulting PAS. It is accordingly desirable to avoid the temperature that significantly causes such undesirable side reactions. The heating temperature likely to suppress such undesirable side reactions is, for example, equal to or higher than 180° C., is preferably equal to or higher than 200° C. and is more preferably equal to or higher than 250° C. The above heating temperature is also, for example, equal to or lower than 400° C., is preferably equal to or lower than 380° C. and is more preferably equal to or lower than 360° C. When a certain degree of side reactions does not cause any substantial trouble, on the other hand, the temperature range of not lower than 250° C. or preferably of not lower than 280° C. is also selectable. The temperature range of not higher than 450° C. or preferably of not higher than 420° C. is also selectable. Such temperature range has the advantage of achieving conversion to a polymer of high degree of polymerization in a very short time.

The time of the above heating differs depending on various characteristics, such as the content rate, the repeating numbers m and the molecular weight, of the cyclic PAS included in the PAS prepolymer used and conditions including the heating temperature and is thus not unequivocally specified. It is, however, preferable to set such a heating time that minimizes the undesirable side reactions described above. The heating time is, for example, equal to or more than 0.05 hours and is preferably equal to or more than 0.1 hours. The heating time is also, for example, equal to or less than 100 hours, is preferably equal to or less than 20 hours and is more preferably equal to or less than 10 hours. The heating time of less than 0.05 hours is likely to cause insufficient conversion of the PAS prepolymer to the PAS. The heating time of more than 100 hours is, on the other hand, likely to cause adverse effects of the undesirable side reactions on the properties of the resulting PAS and may also suffer economic disadvantage.

A variety of catalyst components accelerating conversion may be used in the process of conversion of the PAS prepolymer to the polymer of high degree of polymerization by heating. The catalyst component may be, for example, an ionic compound or a compound having a radical-generating ability. Available examples of the ionic compound include sodium salt and lithium salt of thiophenol and alkali metal salt of sulfur. The compound having the radical-generating ability is, for example, a compound generating a sulfur radical by heating and is more specifically a disulfide bond-containing compound. In applications using the variety of catalyst components, the catalyst component is generally incorporated in the PAS, so that the resulting PAS often contains the catalyst component. Especially in applications using an ionic compound containing an alkali metal and/or another metal component as the catalyst component, most part of the metal component included in this catalyst component is inclined to remain in the resulting PAS. The PAS produced by using the variety of catalyst components is inclined to increase the weight loss in the course of heating the PAS. Accordingly, in order to obtain the PAS of the higher purity and/or the PAS having the less weight loss in the course of heating, it is desirable to minimize the amount of the catalyst component used or preferably to use no catalyst component. In applications using the variety of catalyst components for conversion of the PAS prepolymer to the polymer of high degree of polymerization, it is preferable to adjust the addition amount of the catalyst component, such that the amount of the alkali metal in the reaction system including the PAS prepolymer and the catalyst component is not more than 100 ppm, is preferably not more than 50 ppm, is more preferably not more than 30 ppm and is furthermore preferably not more than 10 ppm and that the weight fraction of sulfur atom forming the disulfide group to the overall weight of all sulfur atoms in the reaction system is less than 1% by weight, is preferably less than 0.5% by weight, is more preferably less than 0.3% by weight and is furthermore preferably less than 0.1% by weight.

Conversion of the PAS prepolymer to the polymer of high degree of polymerization by heating is generally performed in the absence of a solvent but may be performed in the presence of a solvent. The solvent is not specifically limited but may be any solvent that does not substantially interfere with the conversion of the PAS prepolymer to the polymer of high degree of polymerization by heating or does not substantially cause undesirable side reactions, such as degradation and cross-linking of the resulting PAS. Available examples of the solvent include: nitrogen-containing polar solvents such as N-methyl-2-pyrrolidone, dimethylformamide and dimethylacetamide; sulfoxide and sulfone solvents such as dimethyl sulfoxide and dimethyl sulfone; ketone solvents such as acetone, methyl ethyl ketone, diethyl ketone and acetophenone; ether solvents such as dimethyl ether, dipropyl ether and tetrahydrofuran; halogenated solvents such as chloroform, methylene chloride, trichloroethylene, ethylene dichloride, dichloroethane, tetrachloroethane and chlorobenzene; alcohol and phenol solvents such as methanol, ethanol, propanol, butanol, pentanol, ethylene glycol, propylene glycol, phenol, cresol and polyethylene glycol; and aromatic hydrocarbon solvents such as benzene, toluene and xylene. A supercritical fluid of an inorganic compound such as carbon dioxide, nitrogen or water may also be used as the solvent. One of these solvents or a mixture of two or more of these solvents may be used.

The conversion of the PAS prepolymer to the polymer of high degree of polymerization by heating described above may be not only performed using a general polymerization reaction device but performed without limitation using any device equipped with a heating mechanism, for example, performed in a mold for producing a molded product or performed using an extruder or a melt kneader. A known technique such as batch system or continuous system may be employed for such conversion.

The conversion of the PAS prepolymer to the polymer of high degree of polymerization is preferably performed in a non-oxidizing atmosphere and is also preferably performed under reduced pressure condition. When the conversion is performed under reduced pressure, a preferable procedure controls the atmosphere in the reaction system first to the non-oxidizing atmosphere and then to the reduced pressure condition. This is inclined to suppress undesirable side reactions, such as cross-linking reaction and degradation reaction of the PAS prepolymer, of the resulting PAS produced by heating and between the resulting PAS produced by heating and the PAS prepolymer. The non-oxidizing atmosphere herein indicates an atmosphere having the oxygen concentration of not higher than 5% by volume, preferably having the oxygen concentration of not higher than 2% by volume and more preferably having no substantial content of oxygen in the gas phase to which the PAS content is exposed, and specifically an inert gas atmosphere such as nitrogen, helium or argon. Among them, nitrogen atmosphere is especially preferable in terms of the economic efficiency and the easiness of handling. The reduced pressure condition herein indicates that the pressure in the reaction system is lower than the atmospheric pressure. The upper limit is preferably not higher than 50 kPa, is more preferably not higher than 20 kPa and is furthermore preferably not higher than 10 kPa. The lower limit is, for example, not lower than 0.1 kPa and is more preferably not lower than 0.2 kPa. The reduced pressure condition of higher than the preferable upper limit is inclined to cause the undesirable side reactions such as cross-linking reaction. The reduced pressure condition of lower than the preferable lower limit is, on the other hand, inclined to accelerate vaporization of low molecular-weight cyclic polyarylene sulfide included in the PAS prepolymer at some reaction temperatures.

The conversion of the PAS prepolymer to the polymer of high degree of polymerization described above may be performed under coexistence of a fibrous material. The fibrous material herein is a slender threadlike material and is preferably any material of elongated structure, such as natural fibers. The conversion of the PAS prepolymer to the polymer of high degree of polymerization in the presence of the fibrous material facilitates production of a composite material structure of the PAS and the fibrous material. This structure is reinforced by the fibrous material and is thus inclined to have, for example, the better mechanical properties, compared with the PAS alone.

Among a variety of fibrous materials, it is preferable to use a long-fibrous reinforced fiber. This enables the PAS to be highly reinforced. In general, in the case of production of a composite material structure of a resin and a fibrous material, the high viscosity of the resin in the molten state is inclined to reduce the wettability between the resin and the fibrous material, which may fail to produce a homogeneous composite material or fail to provide expected mechanical properties. The wettability herein means a contact between a fluid material like a molten resin and a solid substrate such as a fibrous compound provided and kept in the good physical state without causing substantially no air or another gas to be trapped between the fluid material and the solid substrate. The lower viscosity of the fluid material is inclined to provide the better wettability with the fibrous material. The PAS prepolymer according to an exemplary embodiment of the invention has the significantly low viscosity in the molten state, compared with general thermoplastic resins, for example, PAS manufactured by the conventionally known method, and is thus likely to have the good wettability with the fibrous material. After achieving the good wettability between the PAS prepolymer and the fibrous material, the production method of the PAS according to an exemplary embodiment of the invention converts the PAS prepolymer to the polymer of high degree of polymerization. This facilitates production of the composite material structure in which the fibrous material and the polymer of high degree of polymerization (polyarylene sulfide) have the good wettability.

The fibrous material is preferably the long-fibrous reinforced fiber as described above. The reinforced fiber used according to the invention is not specifically limited, but the reinforced fiber favorably used may be a fiber of high heat resistance and high tensile strength generally used as high-performance reinforced fiber. Examples of such reinforced fiber include glass fibers, carbon fibers, graphite fibers, aramid fibers, silicon carbide fibers, alumina fibers and boron fibers. Among them, most preferable are carbon fibers and graphite fibers which have high specific strength and high specific modulus and are expected to significantly contribute to weight reduction. The carbon fiber and the graphite fiber used may be any types of carbon fibers and graphite fibers according to their applications, but most suitable is a high-strength, high-elongation carbon fiber having the tensile strength of 450 kgf/mm and the tensile elongation of not less than 1.6%. In the case of using the long-fibrous reinforced fiber, the fiber length is preferably 5 cm or longer. This range of the fiber length facilitates the strength of the reinforced fiber to be sufficiently provided in the composite material. The carbon fiber or the graphite fiber used may be mixed with another reinforced fiber. There is no limitation in shape or arrangement of the reinforced fiber. For example, the arrangement of the reinforced fiber used may be a unidirectional arrangement, a random directional arrangement, a sheet-like arrangement, a mat-like arrangement, a fabric-like arrangement, a braid-like arrangement. In applications that need high specific strength and high specific modulus, the reinforced fiber in the unidirectional arrangement is most suitable. The easily-handled reinforced fiber in the cloth (fabric)-like arrangement is also suitable for the invention.

The conversion of the PAS prepolymer to the polymer of high degree of polymerization described above may also be performed in the presence of a filler. The filler used herein may be, for example, non-fibrous glass, non-fibrous carbon or an inorganic filler such as calcium carbonate, titanium oxide or alumina.

EXAMPLES

The invention is described more specifically with reference to examples. These examples are, however, only illustrative and not restrictive. The description first regards evaluation methods of samples obtained by production methods of cyclic polyarylene sulfides in respective examples and comparative examples.

<Analysis of Cyclic Polyphenylene Sulfide>

Qualitative and quantitative analyses of the cyclic polyphenylene sulfide compound were performed by high-performance liquid chromatography (HPLC). Measurement conditions of HPLC were as follows:

Apparatus: LC-10 Avp Series manufactured by Shimadzu Corporation

Column: Mightysil RP-18 GP150-4.6 (5 μm) manufactured by Kanto Chemical Co., Inc.

Detector: photodiode array detector (wavelength: 270 nm)

The structures of the respective components after component separation by HPLC were determined by liquid chromatography-mass spectrometry (LC-MS), matrix-assisted laser desorption/ionization mass spectrometry (MALDI-MS) of fractions obtained by preparative liquid chromatography (preparative LC), nuclear magnetic resonance spectroscopy (NMR) and infrared spectroscopy (IR spectroscopy). The results of such analyses prove that cyclic polyphenylene sulfides having the repeating numbers of 4 to 15 are qualitatively and quantitatively measurable by HPLC under the above conditions.

Peaks detected by the above HPLC analysis were classified into peaks attributed to cyclic polyphenylene sulfide and peaks attributed to the other substances. The ratio (area ratio) of the integral value of the areas of the detected peaks attributed to the substances other than cyclic polyphenylene sulfide to the integral value of the areas of all the detected peaks was defined as the impurity rate. Comparison was made with respect to the amount of impurities in the cyclic polyphenylene sulfide.

<Analysis of Dihalogenated Aromatic Compound>

Quantitative determination of the dihalogenated aromatic compound (quantitative determination of p-dichlorobenzene) in a reaction mixture, in a reaction product and in an intermediate product in the middle of the reaction was performed by gas chromatography under the following conditions:

Apparatus: GC-2010 manufactured by Shimadzu Corporation

Column: J&W DB-5, 0.32 mm×30 m (0.25 μm) manufactured by Agilent Technologies, Inc.

Carrier gas: helium

Detector: flame ionization detector (FID)

<Analysis of Sulfidizing Agent>

Quantitative determination of the sulfidizing agent (quantitative determination of sodium hydrosulfide) in the reaction mixture, in the reaction product and in the intermediate product in the middle of the reaction was performed by ion chromatography under the following conditions:

Apparatus: HIC-20Asuper manufactured by Shimadzu Corporation

Column: Shim-pack IC-SA2 (250 mm×46 mm ID) manufactured by Shimadzu Corporation

Detector: conductivity detector (suppressor)

Eluent: 4.0 mM sodium hydrogen carbonate/1.0 mM sodium carbonate aqueous solution Flow rate: 1.0 mL/minute Injection volume: 50 microliters Column temperature: 30° C.

The procedure added a hydrogen peroxide solution to each sample to oxidize sulfide ion included in the sample to sulfate ion and then determined the quantity of sulfate ion by the above analysis. The procedure subsequently subtracted the quantitative value of sulfate ion by analysis of a corresponding untreated sample without addition of the hydrogen peroxide solution from the determined quantitative value of sulfate ion to calculate the quantity of sulfide ion in the sample. It is contemplated herein that the calculated quantity of sulfide ion corresponds to the amount of unreacted sulfidizing agent included in the sample. The procedure accordingly determined the amount of unreacted sulfidizing agent from the calculated quantity of sulfide ion and calculated the reaction consumption rate of the sulfidizing agent in the sample as the ratio of the determined amount of unreacted sulfidizing agent to the fed amount of the sulfidizing agent.

<Evaluation of Solid-Liquid Separability of Reaction Product>

The solid-liquid separability of the reaction product was evaluated under the following conditions.

The procedure fractionated 200 g of the resulting reaction product and placed the fraction in a 300 mL-volume flask. The reaction product was stirred with a magnetic stirrer and was heated to 100° C. in an oil bath with nitrogen bubbling in the slurry of reaction product.

The procedure set a membrane filter made of polytetrafluoroethylene (PTFE) having the diameter of 90 mm and the mean pore size of 10 μm in a universal filter holder with a tank manufactured by ADVANTEC Co., Ltd. KST-90-UH (effective filtration area: about 45 cm$^2$) and adjusted the temperature of the tank to 100° C. with a band heater.

The procedure placed the reaction product heated to 100° C. in the tank, sealed the tank and pressurized inside of the tank to 0.1 MPa with nitrogen. The procedure measured the time required for discharging 50 g of filtrate since the start time when the filtrate started discharging from the lower portion of the filter holder after pressurization and calculated the filtration rate (kg/(m$^2$·hr)) per unit filtration area.

<Measurement of Molecular Weight of Linear Polyphenylene Sulfide>

The weight-average molecular weight of the linear polyphenylene sulfide used as the raw material was measured under the following conditions and was determined as a value of standard polystyrene equivalent:

Apparatus: SSC-7100 manufactured by Senshu Scientific Co., Ltd.
Column: Shodex UT806M×2
Column temperature: 210° C.
Mobile phase: 1-chloronaphthalene
Detector: differential refractive index detector
Detector temperature: 210° C.

The following describes the production methods of cyclic polyarylene sulfides in respective examples and comparative examples and the results of evaluation of the respective examples and comparative examples. The production conditions and the evaluation results of Examples 1 to 11 and Comparative Examples 1 to 7 are summarized in Table 1.

TABLE 1

|  | Process 1 | | Process 2 | Evaluation Results | | | |
|---|---|---|---|---|---|---|---|
|  | Arylene unit/ 1 mol of sulfur content (mol) | Consumption rate (%) of sulfidizing agent | Arylene unit/ 1 mol of sulfur content (mol) | Formation rate (%) of cyclic PAS | Filtration rate (kg/(hr·m$^2$)) | Content of cyclic PAS (wt %) | Impurity rate (wt %) |
| EX 1 | 1.00 | 94 | 1.10 | 17.8 | 355 | 86 | 2.0 |
| EX 2 | 1.00 | 94 | 1.05 | 17.5 | 247 | 84 | 1.5 |
| EX 3 | 1.00 | 94 | 1.075 | 18.0 | 290 | 84 | 1.5 |
| EX 4 | 1.00 | 94 | 1.25 | 17.4 | 334 | 82 | 4.3 |
| EX 5 | 0.95 | 92 | 1.10 | 18.9 | 600 | 87 | 2.0 |
| EX 6 | 0.90 | 91 | 1.10 | 20.5 | 940 | 87 | 3.5 |
| EX 7 | 0.90 | 91 | 1.10 | 21.1 | 320 | 88 | 2.1 |
| EX 8 | 0.90 | 82 | 1.10 | 18.0 | 260 | 85 | 4.5 |
| EX 9 | 1.02 | 94 | 1.10 | 17.6 | 370 | 86 | 2.1 |
| EX 10 | 0.90 | 91 | 1.10 | 20.6 | 945 | 88 | 3.2 |
| EX 11 | 0.90 | 91 | 1.10 | 20.5 | 935 | 87 | 3.3 |
| COMP EX 1 | 1.00 | 94 | 1.00 | 15.6 | 3 | 79 | 1.5 |
| COMP EX 2 | 1.10 | 95 | 1.10 | 16.0 | 350 | 72 | 10.1 |
| COMP EX 3 | 1.00 | 94 | 1.02 | 17.2 | 9 | 79 | 1.3 |
| COMP EX 4 | 0.75 | 90 | 1.10 | 14.1 | 98 | 70 | 12.0 |
| COMP EX 5 | 0.90 | 39 | 1.10 | 16.4 | 120 | 80 | 5.1 |
| COMP EX 6 | 1.10 | 95 | 1.25 | 16.2 | 460 | 71 | 10.4 |
| COMP EX 7 | 1.02 | 94 | 1.02 | 17.8 | 12 | 80 | 1.3 |

Example 1

Preparation of Reaction Mixture

In an autoclave (material: SUS316L) with an agitator, a reaction mixture was prepared by mixing 28.1 g of a 48% by weight sodium hydrosulfide aqueous solution (0.241 mol as sodium hydrosulfide) and 21.1 g of a 48% by weight sodium hydroxide aqueous solution (0.253 mol as sodium hydroxide) as the sulfidizing agent (a), 35.4 g (0.241 mol) of p-dichlorobenzene (p-DCB) as the dihalogenated aromatic compound (b), and 600 g (6.05 mol) of N-methyl-2-pyrrolidone (NMP) as the organic polar solvent (c). The water content included in the raw materials was 25.6 g (1.42 mol), and the volume of the solvent per 1 mol of sulfur content in the reaction mixture (per 1 mol of sulfur atom included in sodium hydrosulfide added as the sulfidizing agent) was about 2.43 L. The amount of the arylene unit (equivalent to p-DCB added as the dihalogenated aromatic compound) per 1 mol of sulfur content in the reaction mixture (per 1 mol of sulfur atom included in sodium hydrosulfide added as the sulfidizing agent) was 1.00 mol.

<Process 1>

The process sealed the autoclave after substitution of the inside of the autoclave with nitrogen gas and raised the temperature from room temperature to 200° C. over about 1 hour with stirring at 400 rpm. The process subsequently raised the temperature from 200° C. to 250° C. over about 0.5 hours. The pressure in the reaction vessel in this stage was 1.0 MPa as the gauge pressure. The process kept the temperature at 250° C. for 2 hours to heat and react the reaction mixture.

<Process 2>

The process placed an NMP solution of p-DCB (3.54 g of p-DCB dissolved in 10 g of NMP) in a 100 mL-volume small tank provided in the upper portion of the autoclave via a high-pressure valve. After pressurization of the inside of the small tank to about 1.5 MPa, the process opened a valve in the lower portion of the tank to add the NMP solution of p-DCB to the autoclave. The process washed the wall surface of the small tank with 5 g of NMP and further added this NMP to the autoclave. As the result of these operations, the arylene unit per 1 mol of sulfur content in the reaction mixture (equivalent to the total amount of p-DCB added as the dihalogenated aromatic compound in the process 1 and in the process 2) was 1.10 mol. After completion of this supplementary addition, the reaction proceeded while heating at 250° C. continued for another 1 hour. After decreasing the temperature to 230° C. over about 15 minutes, the process gradually opened the high-pressure valve provided in the upper portion of the autoclave to discharge a vapor mainly made of NMP. The process obtained about 394 g of a liquid component by condensation of this vapor component in a water cooled condenser tube and closed the high-pressure valve to seal the autoclave. The process then rapidly cooled down the autoclave to about room temperature and recovered a reaction product.

<Analytical Evaluation of Reaction Product>

The procedure dispersed part of the obtained reaction product in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 96%. The formation rate of cyclic polyphenylene sulfide was 17.8% relative to the formation rate on the assumption that the sulfidizing agent in the reaction mixture was fully converted to cyclic polyphenylene sulfide. As the evaluation result of the solid-liquid separability of the obtained reaction product, the filtration rate was 355 kg/(m²·hr).

<Recovery of Cyclic Polyarylene Sulfide>

The procedure placed 100 g of a filtrate component obtained by solid-liquid separation of the reaction product in the same manner as the above evaluation of the solid-liquid separability, in a 300 mL flask and substituted the inside of the flask with nitrogen. The procedure then heated the reaction product to 100° C. and subsequently cooled the reaction product to 80° C., with stirring. Although a partly insoluble component was present at ordinary temperature, no insoluble component was observed in the stage heated to 100° C. and in the stage cooled to 80° C. The procedure then slowly added 33 g of water dropwise with a tube pump over about 15 minutes, while stirring the reaction product at the temperature of 80° C. in the system. The weight ratio of NMP to water in the filtrate mixture after dropwise addition of water was 75 to 25. In the process of addition of water to the filtrate, the temperature of the mixture was decreased to about 75° C. by dropwise addition of water, and a solid content was gradually produced in the mixture. At the stage that dropwise addition of water was concluded, the mixture was a slurry with the solid content dispersed therein. The procedure cooled the slurry to about 30° C. over about 1 hour with stirring, subsequently continued stirring for about 30 minutes at the temperature of not higher than 30° C., and suction-filtered the resulting slurry through a glass filter with apertures of 10 to 16 µm. An operation of dispersing the resulting solid content (including the mother liquid) in about 30 g of water, stirring the dispersion at 70° C. for 15 minutes, and suction-filtering the dispersion through the glass filter in the same manner as above was repeated a total of four times. A dried solid of cyclic polyarylene sulfide was obtained by treating the resulting solid content at 70° C. in a vacuum dryer for 3 hours.

Analysis of the dried solid by HPLC resulted in detection of cyclic polyphenylene sulfides of the repeating unit numbers of 4 to 15. The content rate of the cyclic polyphenylene sulfide in the dried solid was about 86% by weight, so that the obtained dried solid was identified as high purity cyclic polyphenylene sulfide. The impurity rate of this dried solid was 2.0%.

A sample obtained by recovery of the reaction mixture at the end of the process 1 when the series of operations was terminated was also provided, separately from the sample obtained by recovery of the reaction product after solid-liquid separation subsequent to the process 1 and the process 2 as described above. As the result of analysis of this reaction mixture, the reaction consumption rate of sodium hydrosulfide was 94% at the end of the process 1. This proves that the process 2 was performed after the sulfidizing agent included in the reaction mixture was sufficiently consumed for the reaction.

The results of Example 1 show that the production method of the cyclic polyarylene sulfide of the invention allowed for production of high-quality cyclic polyarylene sulfide having a low impurity content rate at a high yield. These results also indicate the extremely high efficiency of solid-liquid separation in the manufacturing process of the cyclic PAS and the remarkably high productivity.

Comparative Example 1

The same series of operations as those of Example 1 were performed in the process 2, except that only 15 g of NMP was supplementarily added to the autoclave using the small tank without supplementary addition of DCB in the process 2 of Example 1. Accordingly, the arylene unit per 1 mol of sulfur content in the reaction mixture was 1.00 mol in both the process 1 and the process 2. The arylene unit per 1 mol of sulfur content in the reaction mixture was thus consistently 1.00 mol from the start to the end of the reaction.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 96%. The formation rate of cyclic polyphenylene sulfide was 15.6% relative to the formation rate on the assumption that the sulfidizing agent in the reaction mixture was fully converted to cyclic polyphenylene sulfide. As the evaluation result of the solid-liquid separability of the obtained reaction product, the filtration rate was 3 kg/(m²·hr).

<Recovery of Cyclic Polyarylene Sulfide>

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 79% by weight. The impurity rate of this dried solid was 1.5%.

The results of Comparative Example 1 show that the resulting cyclic polyarylene sulfide was inclined to have low impurity rate, even when the procedure did not perform supplementary addition of the dihalogenated aromatic compound, which is a preferred characteristic of the present invention, to have a different ratio of the arylene unit to 1 mol of sulfur content in the reaction mixture in the process 2 from that of the present invention. Comparative Example 1, however, had the low weight fraction of the cyclic polyarylene sulfide (content rate of cyclic PAS) in the isolated dried solid and additionally had the poor solid-liquid separability and the low productivity of the reaction product.

Comparative Example 2

The same series of operations as those of Example 1 were performed in the process 1, except that 38.9 g (0.265 mol) of p-DCB was added in preparation of the reaction mixture of Example 1 to adjust the arylene unit to 1.10 mol per 1 mol of sulfur content in the reaction mixture.

The process 2 employed the same series of operations as those of Comparative Example 1. Specifically, the process 2 supplementarily added only 15 g of NMP to the autoclave using the small tank without supplementary addition of p-DCB. While p-DCB was not supplementarily added in the process 2 of Comparative Example 2, the amount of p-DCB per 1 mol of sulfur content of sodium hydrosulfide in the reaction mixture used in the process 1 was 1.10 mol. The reaction accordingly proceeded under the same condition in the process 2. The amount of p-DCB per 1 mol of sulfur content in the reaction mixture was thus consistently 1.10 mol from the start to the end of the reaction.
<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 97%. The formation rate of cyclic polyphenylene sulfide was 16.0% relative to the formation rate on the assumption that the sulfidizing agent in the reaction mixture was fully converted to cyclic polyphenylene sulfide. As the evaluation result of the solid-liquid separability of the obtained reaction product, the filtration rate was 350 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 72% by weight. The impurity rate of this dried solid was 10.1%.

Like Example 1, the reaction mixture was recovered and analyzed at the end of the process 1 when the series of operations was terminated. As the result of analysis, the reaction consumption rate of sodium hydrosulfide was 95% at the end of the process 1. This proves that the process 2 was performed after the sulfidizing agent included in the reaction mixture was sufficiently consumed for the reaction.

The results of Comparative Example 2 show that the procedure that did not perform supplementary addition of the dihalogenated aromatic compound, which is a preferred characteristic of the present invention, to have a different ratio of the arylene unit to 1 mol of sulfur content in the reaction mixture in the process 1 from that of the present invention allowed for production of only poor-quality cyclic polyarylene sulfide having a very high impurity rate.

Example 2

The process 1 was performed in the same manner as Example 1 (the reaction consumption rate of sodium hydrosulfide was 94% at the end of the process 1). The NMP solution of p-DCB added in the subsequent process 2 was replaced by a solution of 1.76 g of p-DCB dissolved in 10 g of NMP. In other words, cyclic PAS was manufactured under the same conditions as those of Example 1, except that the reaction proceeded in the process 2 with adjustment of the arylene unit to 1.05 mol per 1 mol of sulfur content in the reaction system in the process 2.
<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 96%. The formation rate of cyclic polyphenylene sulfide was 17.5% relative to the formation rate on the assumption that the sulfidizing agent in the reaction mixture was fully converted to cyclic polyphenylene sulfide. As the evaluation result of the solid-liquid separability of the obtained reaction product, the filtration rate was 247 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 84% by weight. The impurity rate of this dried solid was 1.5%.

The results of Example 2 show that the production method of the cyclic polyarylene sulfide of the invention allowed for production of high-quality cyclic polyarylene sulfide having a low impurity content rate at a high yield. These results also indicate the extremely high efficiency of solid-liquid separation in the manufacturing process of the cyclic PAS and the remarkably high productivity. Comparison with Example 1 indicate that the lower setting of the ratio of the arylene unit to 1 mol of sulfur content in the reaction mixture in the process 2 further improved the purity of the resulting cyclic polyarylene sulfide and achieved the extremely high productivity, although slightly decreasing the solid-liquid separability of the reaction product.

Example 3

The process 1 was performed in the same manner as Example 1 (the reaction consumption rate of sodium hydrosulfide was 94% at the end of the process 1). The NMP solution of p-DCB added in the subsequent process 2 was replaced by a solution of 2.65 g of p-DCB dissolved in 10 g of NMP. In other words, cyclic PAS was manufactured under the same conditions as those of Example 1, except that the reaction proceeded in the process 2 with adjustment of the arylene unit to 1.075 mol per 1 mol of sulfur content in the reaction system in the process 2.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 97%. The formation rate of cyclic polyphenylene sulfide was 18.0% relative to the formation rate on the assumption that the sulfidizing agent in the reaction mixture was fully converted to cyclic polyphenylene sulfide. As the evaluation result of the solid-liquid separability of the obtained reaction product, the filtration rate was 290 kg/(m²·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 84% by weight. The impurity rate of this dried solid was 1.5%.

Comparison of the results of Example 3 with those of Example 1 indicates that even the further lower setting of the ratio of the arylene unit to 1 mol of sulfur content in the reaction mixture in the process 2 in the production method of the cyclic polyarylene sulfide of the invention achieved the sufficient levels of the purity of the resulting cyclic polyarylene sulfide and the solid-liquid separability in the manufacturing process of the cyclic PAS.

Example 4

The process 1 was performed in the same manner as Example 1 (the reaction consumption rate of sodium hydrosulfide was 94% at the end of the process 1). The NMP solution of p-DCB added in the subsequent process 2 was replaced by a solution of 8.84 g of p-DCB dissolved in 20 g of NMP. In other words, cyclic PAS was manufactured under the same conditions as those of Example 1, except that the reaction proceeded in the process 2 with adjustment of the arylene unit to 1.25 mol per 1 mol of sulfur content in the reaction system in the process 2.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 99%. The formation rate of cyclic polyphenylene sulfide was 17.4% relative to the formation rate on the assumption that the sulfidizing agent in the reaction mixture was fully converted to cyclic polyphenylene sulfide. As the evaluation result of the solid-liquid separability of the obtained reaction product, the filtration rate was 334 kg/(m²·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 82% by weight. The impurity rate of this dried solid was 4.3%.

Comparison of the results of Example 4 with those of Example 1 indicates that the higher setting of the ratio of the arylene unit to 1 mol of sulfur content in the reaction mixture in the process 2 in the production method of the cyclic polyarylene sulfide of the invention further enhanced the solid-liquid separability of the resulting reaction product in manufacture of the cyclic polyarylene sulfide but was inclined to increase the impurity content included in the resulting cyclic polyarylene sulfide.

Comparative Example 3

Cyclic PAS was manufactured under the same conditions as those of Example 1, except that the NMP solution of p-DCB added in the process 2 was replaced with a solution of 0.71 g of p-DCB dissolved in 10 g of NMP and the reaction proceeded in the process 2 with adjustment of the arylene unit to 1.02 mol per 1 mol of sulfur content in the reaction system in the process 2.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 97%. The formation rate of cyclic polyphenylene sulfide was 17.2% relative to the formation rate on the assumption that the sulfidizing agent in the reaction mixture was fully converted to cyclic polyphenylene sulfide. As the evaluation result of the solid-liquid separability of the obtained reaction product, the filtration rate was 9 kg/(m²·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 79% by weight. The impurity rate of this dried solid was 1.3%.

The results of Comparative Example 3 show that addition of the dihalogenated aromatic compound after the process 1 was still inclined to obtain cyclic polyarylene sulfide of the low impurity rate under the condition that the ratio of the arylene unit to 1 mol of sulfur content in the reaction mixture in the process 2 was lower than the preferred range of the present invention. This, however, resulted in the low content rate of the cyclic polyarylene sulfide in the isolated dried solid and furthermore resulted in the poor solid-liquid separability and the low productivity in the manufacturing process of the cyclic PAS.

Example 5

The same series of operations as those of Example 1 were performed in the process 1, except that 33.6 g (0.229 mol) of p-DCB was added in preparation of the reaction mixture of Example 1 to adjust the arylene unit to 0.95 mol per 1 mol of sulfur content in the reaction mixture. The NMP solution of p-DCB added in the subsequent process 2 was replaced by a solution of 5.31 g of p-DCB dissolved in 10 g of NMP. In other words, cyclic PAS was manufactured under the same conditions as those of Example 1, except that the reaction proceeded in the process 1 with adjustment of the arylene unit to 0.95 mol per 1 mol of sulfur content in the reaction system in the process 1.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 97%. The formation rate of cyclic polyphenylene sulfide was 18.9% relative to the formation rate on the assumption that the sulfidizing agent in the reaction mixture was fully converted to cyclic polyphenylene sulfide. As the evaluation result of the solid-liquid separability of the obtained reaction product, the filtration rate was 600 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 87% by weight. The impurity rate of this dried solid was 2.0%.

The reaction mixture was recovered and analyzed at the end of the process 1 when the series of operations was terminated. As the result of analysis, the reaction consumption rate of sodium hydrosulfide was 92% at the end of the process 1. This proves that the process 2 was performed after the sulfidizing agent included in the reaction mixture was sufficiently consumed for the reaction.

The results of Example 5 show that setting the excess sulfur condition to the ratio of the arylene unit to 1 mol of sulfur content in the reaction mixture in the process 1 in the production method of the cyclic polyarylene sulfide of the invention improved the formation rate of the cyclic polyarylene sulfide.

Example 6

The same series of operations as those of Example 1 were performed in the process 1, except that 31.8 g (0.217 mol) of p-DCB was added in preparation of the reaction mixture of Example 1 to adjust the arylene unit to 0.90 mol per 1 mol of sulfur content in the reaction mixture. The NMP solution of p-DCB added in the subsequent process 2 was replaced by a solution of 7.07 g of p-DCB dissolved in 10 g of NMP. In other words, cyclic PAS was manufactured under the same conditions as those of Example 1, except that the reaction proceeded in the process 1 with adjustment of the arylene unit to 0.90 mol per 1 mol of sulfur content in the reaction system in the process 1.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 97%. The formation rate of cyclic polyphenylene sulfide was 20.5% relative to the formation rate on the assumption that the sulfidizing agent in the reaction mixture was fully converted to cyclic polyphenylene sulfide. As the evaluation result of the solid-liquid separability of the obtained reaction product, the filtration rate was 940 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 87% by weight. The impurity rate of this dried solid was 3.5%.

The reaction mixture was recovered and analyzed at the end of the process 1 when the series of operations was terminated. As the result of analysis, the reaction consumption rate of sodium hydrosulfide was 91% at the end of the process 1. This proves that the process 2 was performed after the sulfidizing agent included in the reaction mixture was sufficiently consumed for the reaction.

The results of Example 6 show that setting the more excess sulfur condition than the condition of Example 5 to the ratio of the arylene unit to 1 mol of sulfur content in the reaction mixture in the process 1 in the production method of the cyclic polyarylene sulfide of the invention further improved the formation rate of the cyclic polyarylene sulfide but slightly increased the impurity rate.

Example 7

After performing the same series of operations as those of Example 6 in the process 1 (the reaction consumption rate of sodium hydrosulfide was 91% at the end of the process 1), the procedure placed an NMP solution of p-DCB (3.54 g of p-DCB dissolved in 10 g of NMP) in a 100 mL-volume small tank provided in the upper portion of the autoclave via a high-pressure valve. After pressurization of the inside of the small tank to about 1.5 MPa, the process opened a valve in the lower portion of the tank to add the NMP solution of p-DCB to the autoclave. The process washed the wall surface of the small tank with 5 g of NMP and further added this NMP to the autoclave. As the result of these operations, the arylene unit per 1 mol of sulfur content in the reaction mixture was 1.00 mol. The series of operations for this supplementary addition took about 5 minutes. After completion of this supplementary addition, the reaction proceeded while heating at 250° C. continued for another 0.5 hours. The reaction in the process 2 was performed in the same manner as Example 6, except that the NMP solution of p-DCB added in the subsequent process 2 was replaced by a solution of 3.53 g of p-DCB dissolved in 10 g of NMP to adjust the arylene unit to 1.10 mol per 1 mol of sulfur content in the reaction system in the process 2.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 98%. The formation rate of cyclic polyphenylene sulfide was 21.1% relative to the formation rate on the assumption that the sulfidizing agent in the reaction mixture was fully converted to cyclic polyphenylene sulfide. As the evaluation result of the solid-liquid separability of the obtained reaction product, the filtration rate was 320 kg/($m^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 88% by weight. The impurity rate of this dried solid was 2.1%.

The results of Example 7 show that setting the excess sulfur condition to the ratio of the arylene unit to 1 mol of sulfur content in the reaction mixture in the process 1 in the production method of the cyclic polyarylene sulfide of the invention and employing fractional addition as the technique of addition of DCB, which is the especially preferable technique in the invention, further improved the formation rate of the cyclic polyarylene sulfide and allowed for production of high-quality cyclic polyarylene sulfide having a low impurity rate.

Comparative Example 4

The same series of operations as those of Example 1 were performed in the process 1, except that 26.5 g (0.181 mol) of p-DCB was added in preparation of the reaction mixture of Example 1 to adjust the arylene unit to 0.75 mol per 1 mol of sulfur content in the reaction mixture. The process 2 was performed under the same conditions as those of Example 1, except that the NMP solution of p-DCB added in the process 2 was replaced by a solution of 12.4 g of p-DCB dissolved in 10 g of NMP to adjust the arylene unit to 1.10 mol per 1 mol of sulfur content in the reaction system in the process 2.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 97%. The formation rate of cyclic polyphenylene sulfide was 14.1% relative to the formation rate on the assumption that the sulfidizing agent in the reaction mixture was fully converted to cyclic polyphenylene sulfide. As the evaluation result of the solid-liquid separability of the obtained reaction product, the filtration rate was 98 kg/($m^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 70% by weight. The impurity rate of this dried solid was 12.0%.

The reaction mixture was recovered and analyzed at the end of the process 1 when the series of operations was terminated. As the result of analysis, the reaction consumption rate of sodium hydrosulfide was 90% at the end of the process 1. This proves that the process 2 was performed after the sulfidizing agent included in the reaction mixture was sufficiently consumed for the reaction.

The results of Comparative Example 4 show that the lower setting of the ratio of the arylene unit to 1 mol of sulfur content in the reaction mixture in the process 1 than the preferred range of the invention in the production method of the cyclic polyarylene sulfide of the invention caused the low formation rate of the cyclic polyarylene sulfide and the significantly increased impurity rate and resulted in production of only low-quality cyclic polyarylene sulfide.

Comparative Example 5

The same series of operations as those of Example 6 were performed, except that the heating conditions in the process 1 were changed to the conditions of raising the temperature to 200° C. and keeping the temperature at 200° C. for 2 hours and the operations of the process 2 were performed subsequently.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 95%. The formation rate of cyclic polyphenylene sulfide was 16.4% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 120 kg/($m^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 80% by weight. The impurity rate of this dried solid was 5.1%.

The reaction mixture was recovered and analyzed at the end of the process 1 when the series of operations was terminated. As the result of analysis, the reaction consumption rate of sodium hydrosulfide was 39% at the end of the process 1. This indicates that the process 2 was performed prior to sufficient reaction consumption of the sulfidizing agent included in the reaction mixture, i.e., in the stage of insufficient reaction consumption of the sulfidizing agent.

The results of Comparative Example 5 show that supplementary addition of the dihalogenated aromatic compound, which is a preferred characteristic of the invention, prior to reaction consumption of 50% or more of the sulfidizing agent, i.e., in the state of insufficient reaction consumption of the sulfidizing agent caused the low formation rate of cyclic polyarylene sulfide and resulted in production of only poor-quality cyclic polyarylene sulfide having the high impurity rate.

Example 8

The same series of operations as those of Example 6 were performed, except that the process 1 was terminated at the time when the temperature was raised to 250° C. and the operations of the process 2 were performed subsequently.
<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 95%. The formation rate of cyclic polyphenylene sulfide was 18.0% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 260 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 85% by weight. The impurity rate of this dried solid was 4.5%.

The reaction mixture was recovered and analyzed at the end of the process 1 when the series of operations was terminated. As the result of analysis, the reaction consumption rate of sodium hydrosulfide was 82% at the end of the process 1. This proves that the process 2 was performed after the sulfidizing agent included in the reaction mixture was sufficiently consumed for the reaction.

The results of Example 8 show that the production method of the cyclic polyarylene sulfide of the invention in Example 8 had the slightly lower reaction consumption rate of the sulfidizing agent at the end of the process 1 than that of Example 6, which caused some decrease in solid-liquid separability of the resulting reaction product in manufacture of the cyclic polyarylene sulfide but still maintained the high productivity. The resulting cyclic polyarylene sulfide had sufficiently high quality with slight reduction in formation rate and quality.

Example 9

The same series of operations as those of Example 1 were performed in the process 1, except that 36.1 g (0.246 mol) of p-DCB was added in preparation of the reaction mixture of Example 1 to adjust the arylene unit to 1.02 mol per 1 mol of sulfur content in the reaction mixture. The process 2 was performed under the same conditions as those of Example 1, except that the NMP solution of p-DCB added in the process 2 was replaced by a solution of 2.87 g of p-DCB dissolved in 10 g of NMP to adjust the arylene unit to 1.10 mol per 1 mol of sulfur content in the reaction system in the process 2.
<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 98%. The formation rate of cyclic polyphenylene sulfide was 17.6% relative to the formation rate on the assumption that the sulfidizing agent in the reaction mixture was fully converted to cyclic polyphenylene sulfide. As the evaluation result of the solid-liquid separability of the obtained reaction product, the filtration rate was 370 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 86% by weight. The impurity rate of this dried solid was 2.1%.

The reaction mixture was recovered and analyzed at the end of the process 1 when the series of operations was terminated. As the result of analysis, the reaction consumption rate of sodium hydrosulfide was 94% at the end of the process 1. This proves that the process 2 was performed after the sulfidizing agent included in the reaction mixture was sufficiently consumed for the reaction.

The results of Example 9 show that a slight increase in ratio of the arylene unit to 1 mol of sulfur content in the reaction mixture in the process 1 from 1.00 mol to 1.02 mol in the production method of the cyclic polyarylene sulfide of the invention provided substantially equivalent results, for example, the purity of the cyclic polyarylene sulfide, to those of Example 1 but was inclined to improve the efficiency of solid-liquid separation of the resulting reaction product in manufacture.

Comparative Example 6

The same series of operations as those of Example 4 were performed in the process 1, except that 38.9 g (0.264 mol) of p-DCB was added in preparation of the reaction mixture of Example 4 to adjust the arylene unit to 1.10 mol per 1 mol of sulfur content in the reaction mixture. The process 2 was performed under the same conditions as those of Example 1, except that the NMP solution of p-DCB added in the process 2 was replaced by a solution of 5.38 g of p-DCB dissolved in 20 g of NMP to adjust the arylene unit to 1.25 mol per 1 mol of sulfur content in the reaction system in the process 2.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 97%. The formation rate of cyclic polyphenylene sulfide was 16.2% relative to the formation rate on the assumption that the sulfidizing agent in the reaction mixture was fully converted to cyclic polyphenylene sulfide. As the evaluation result of the solid-liquid separability of the obtained reaction product, the filtration rate was 460 kg/(m²·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 71% by weight. The impurity rate of this dried solid was 10.4%.

The reaction mixture was recovered and analyzed at the end of the process 1 when the series of operations was terminated. As the result of analysis, the reaction consumption rate of sodium hydrosulfide was 95% at the end of the process 1. This proves that the process 2 was performed after the sulfidizing agent included in the reaction mixture was sufficiently consumed for the reaction.

The results of Comparative Example show that the relatively high setting of the ratio of the arylene unit to 1 mol of sulfur content in the reaction mixture in the process 1 and in the process 2 in the production method of the cyclic polyarylene sulfide of the invention was inclined to increase the impurity content included in the resulting cyclic polyarylene sulfide, while further enhancing the solid-liquid separability of the resulting reaction product in manufacture of the cyclic polyarylene sulfide.

Reference Example 1

The following describes a method of preparing a sulfidizing agent of the reduced water content by dehydration of a water-containing sulfidizing agent used as the raw material in an organic polar solvent.

In a 1 liter autoclave with an agitator, 28.1 g of a 48% by weight sodium hydrosulfide aqueous solution (0.241 mol as sodium hydrosulfide), 19.8 g of a 48% by weight sodium hydroxide aqueous solution (0.238 mol as sodium hydroxide) and 238.0 g (2.40 mol) of N-methyl-2-pyrrolidone (NMP) were mixed. The mixture placed in the autoclave corresponds to the water-containing sulfidizing agent. The water content included in the raw material was 24.9 g (1.38 mol), and the amount of water per 1 mol of sulfur content in the sulfidizing agent was 5.75 mol. The volume of the organic polar solvent per 1 mol of sulfur content in the sulfidizing agent was about 0.97 liters.

A rectifying column filled with a filler was attached to the upper portion of the autoclave via a valve. Deliquoring was performed by gradually heating the mixture to 230° C. over about 3 hours with stirring at 240 rpm and flowing nitrogen under ordinary pressure. This gave 27.1 g of distillate.

This distillate was analyzed by gas chromatography. The composition of the distillate included 23.4 g of water and 3.7 g of NMP. This indicates that 1.5 g (0.083 mol) of water and 234.3 g (2.36 mol) of NMP remained in the reaction mixture in the reaction system at this stage. Hydrogen sulfide released from the reaction system through the deliquoring process was 0.004 mol. This shows a decrease in sodium hydrosulfide by 0.004 mol and an increase in sodium hydroxide by 0.004 mol in the reaction system by the release of hydrogen sulfide.

The procedure then cooled down the inside of the autoclave to about room temperature and recovered the semisolid content. The results of the above analysis show that the recovered content was a sulfidizing agent of the reduced water content, including 0.237 mol of sodium hydrosulfide, 0.242 mol of sodium hydroxide, 0.083 mol of water and 234.3 g (2.36 mol) of NMP.

Reference Example 2

The following describes a method of preparing a slurry of a raw material mixture by mixing a sulfidizing agent, p-DCB and NMP.

In a stainless steel autoclave with an agitator, 218.36 g of the sulfidizing agent of the reduced water content obtained in Reference Example 1 (consisting of 11.21 g (0.200 mol) of sodium hydrosulfide, 8.17 g (0.204 mol) of sodium hydroxide, 1.26 g (0.070 mol) of water and 197.72 g (1.997 mol) of N-methyl-2-pyrrolidone (NMP)), 29.99 g (0.204 mol) of p-dichlorobenzene (p-DCB), and 386.53 g (3.90 mol) of N-methyl-2-pyrrolidone (NMP) were mixed. The volume of the solvent per 1 mol of sulfur content in the fed raw material mixture was about 2.85 liters. The arylene unit per 1 mol of sulfur content was 1.02 mol. The fed raw material mixture was stirred at 100° C. for 30 minutes after the inside of the autoclave was sufficiently substituted with nitrogen. The resulting homogeneous slurry was used as raw material mixture.

Comparative Example 7

The same series of operations as those of Example 9 were performed in the process 1 (the reaction consumption rate of sodium hydrosulfide was 94% at the end of the process 1). The process 2 was performed under the same conditions as those of Example 1, except that the NMP solution of p-DCB added in the process 2 was replaced by 60.75 g of the slurry of raw material mixture (including 0.0195 mol equivalent as the arylene unit and 0.0191 mol equivalent as the sulfur content) prepared in Reference Example 2 to simultaneously add the sulfur content and adjust the arylene unit to 1.02 mol per 1 mol of sulfur content in the reaction system.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by gas chromatography, high-performance liquid chromatography and ion chromatography. The result of such analyses shows that the reaction consumption rate of sodium hydrosulfide used as the sulfidizing agent was 94%. The formation rate of cyclic polyphenylene sulfide was 17.8% relative to the formation rate on the assumption that the sulfidizing agent in the reaction mixture was fully converted to cyclic polyphenylene sulfide. As the evaluation result of the solid-liquid separability of the obtained reaction product, the filtration rate was 12 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 80% by weight. The impurity rate of this dried solid was 1.3%.

This Comparative Example show that simultaneous supplementary addition of the dihalogenated aromatic compound and the sulfidizing agent increased the formation rate of the cyclic polyphenylene sulfide, compared with Example 9, but reduced the solid-liquid separability and deteriorated the quality (reduced the content rate of the cyclic PAS).

Example 10

The same series of operations as those of Example 6 were performed, except that the reaction temperature was raised to 260° C. after the operation of supplementary addition in the process 2.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 97%. The formation rate of cyclic polyphenylene sulfide was 20.6% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 945 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 88% by weight. The impurity rate of this dried solid was 3.2%.

The results of Example 10 show that performing the process 2 at the higher temperature than the process 1 in the production method of the cyclic polyphenylene sulfide of the invention was inclined to improve the content rate of the resulting cyclic polyphenylene sulfide and reduce the impurity rate and resulted in production of high-quality cyclic polyphenylene sulfide.

Example 11

The same series of operations as those of Example 6 were performed, except that the reaction temperature was raised to 270° C. in the process 2.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 98%. The formation rate of cyclic polyphenylene sulfide was 20.5% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 935 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 87% by weight. The impurity rate of this dried solid was 3.3%.

The results of Example 11 show that performing the process 2 at the further higher temperature than Example 10 also resulted in production of high-quality cyclic polyphenylene sulfide. The reaction temperature may thus be raised to 270° C., but such temperature rise did not cause any further improvement in quality.

Reference Example 3

The following describes an example of manufacturing linear polyarylene sulfide by a prior art technique or more specifically by a method of heating and reacting a sulfidizing agent, a dihalogenated aromatic compound and 1.25 liters or more of an organic polar solvent relative to 1 mol of sulfur content in the sulfidizing agent to obtain a reaction mixture and separating a linear polyarylene sulfide from a cyclic polyarylene sulfide by solid-liquid separation of the obtained reaction mixture to produce the linear polyarylene sulfide as the solid content including the solvent.

In a stainless steel autoclave (reaction vessel) with an agitator, 46.75 g of a 48% by weight sodium hydrosulfide aqueous solution (0.40 mol as sodium hydrosulfide), 35.00 g of a 48% by weight sodium hydroxide aqueous solution (0.42 mol), 1000 g (10.1 mol) of NMP and 59.98 g (0.41 mol) of p-dichlorobenzene (p-DCB) were mixed. After the inside of the reaction vessel was sufficiently substituted with nitrogen, the reaction vessel was pressurized to 0.3 MPa as the gauge pressure with pressurized nitrogen and was then sealed.

The procedure raised the temperature in the reaction vessel from room temperature to 200° C. over about 1 hour with stirring at 400 rpm. The pressure in the reaction vessel in this stage was 0.9 MPa as the gauge pressure. The temperature in the reaction vessel was subsequently raised from 200° C. to 250° C. over about 30 minutes. The pressure in the reaction vessel in this stage was 1.5 MPa as the gauge pressure. The procedure kept the temperature at 250° C. for 2 hours, rapidly decreased the temperature to about room temperature and recovered the content from the reaction vessel.

As the result of analysis of the resulting content by gas chromatography and high-performance liquid chromatography, the consumption rate of p-DCB monomer was 92%. The formation rate of cyclic polyarylene sulfide was 16.7% relative to the formation rate on the assumption that the entire sulfur content in the reaction mixture was converted to cyclic polyarylene sulfide.

The procedure placed the content obtained above or more specifically the reaction mixture including at least cyclic polyarylene sulfide, linear polyarylene sulfide, NMP and NaCl as a byproduct salt in a recovery flask, sufficiently substituted the inside of the flask with nitrogen, subsequently adjusted the temperature to about 100° C. with stirring and performed solid-liquid separation of the above reaction mixture by pressure filtration under heating using pressurized nitrogen. This series of operations gave a solid content in the wet state.

The procedure fractionated part of the obtained solid content in the wet state, sufficiently washed the fraction with warm water and subsequently dried the fraction to obtain a dried solid. The results of infrared spectroscopy for absorption spectral analysis show that this dried solid was linear polyphenylene sulfide and the weight-average molecular weight was 11,000 as polystyrene equivalent. It is also shown that the content rate of linear polyphenylene sulfide in the solid content in the wet state was about 23% from the weight of the obtained dried solid. The results of analysis of the above solid content in the wet state also show that the content rate of NMP and the content rate of NaCl were respectively 47% by weight and 30% by weight.

The following describes the production methods of cyclic polyarylene sulfides in respective examples and comparative examples using the reaction mixture further including linear polyarylene sulfide obtained in Reference Example 3, and the results of evaluation of the respective examples and comparative examples. The production conditions and the evaluation results of Examples 12 to 17 and Comparative Examples 8 and 9 are summarized in Table 2.

derived from p-DCB added as the dihalogenated aromatic compound) per 1 mol of sulfur content in the reaction mixture was 1.00 mol.

<Process 1>

The process sealed the autoclave after substitution of the inside of the autoclave with nitrogen gas and raised the temperature from room temperature to 200° C. over about 1 hour with stirring at 400 rpm. The process subsequently raised the temperature from 200° C. to 250° C. over about 0.5 hours. The pressure in the reaction vessel in this stage was 0.5 MPa as the gauge pressure. The process kept the temperature at 250° C. for 1 hour to heat and react the reaction mixture.

<Process 2>

The process placed an NMP solution of p-DCB (1.76 g of p-DCB dissolved in 50 g of NMP) in a 100 mL-volume small tank provided in the upper portion of the autoclave via a high-pressure valve. After pressurization of the inside of the small tank to about 1.5 MPa, the process opened a valve in the lower portion of the tank to add the NMP solution of p-DCB to the autoclave. The process washed the wall surface of the small tank with 10 g of NMP and further added this NMP to the autoclave. As the result of these operations, the arylene unit per 1 mol of sulfur content in the reaction mixture in the reaction system (equivalent to the total amount of the phenylene unit derived from linear polyphenylene sulfide added as the linear polyarylene sulfide in the process 1 and the phenylene unit derived from p-DCB added as the halogenated aromatic compound in the process 1 and in the process 2) was 1.05 mol, and the volume of the solvent per 1 mol of sulfur content in the reaction mixture was 2.74 liters. After comple-

TABLE 2

| | Process 1 | | Process 2 | Evaluation Results | | | |
|---|---|---|---|---|---|---|---|
| | Arylene unit/ 1 mol of sulfur content (mol) | Consumption rate (%) of sulfidizing agent | Arylene unit/ 1 mol of sulfur content (mol) | Formation rate (%) of cyclic PAS | Filtration rate (kg/(hr · m$^2$)) | Content of cyclic PAS (wt %) | Impurity rate (wt %) |
| EX 12 | 1.00 | 75.0 | 1.05 | 15.9 | 55 | 87 | 2.1 |
| EX 13 | 0.98 | 78.0 | 1.05 | 17.0 | 83 | 87 | 1.8 |
| EX 14 | 0.90 | 77.5 | 1.05 | 17.8 | 80 | 86 | 2.3 |
| EX 15 | 0.90 | 77.5 | 1.10 | 18.2 | 155 | 86 | 3.7 |
| EX 16 | 0.90 | 77.5 | 1.10 | 18.6 | 170 | 87 | 3.2 |
| EX 17 | 0.90 | 88.6 | 1.10 | 19.3 | 175 | 87 | 3.1 |
| COMP EX 8 | 1.05 | 68.1 | 1.05 | 10.8 | 15 | 71 | 4.5 |
| COMP EX 9 | 0.90 | 29.4 | 1.10 | 12.5 | 310 | 78 | 5.6 |

Example 12

In an autoclave (material: SUS316L) with an agitator, a reaction mixture was prepared by mixing 90.39 g of the linear polyphenylene sulfide in the wet state obtained in Reference Example 3 (20.79 g as linear polyphenylene sulfide (0.192 mol equivalent respectively as the sulfur content and as the arylene unit), 42.48 g (0.429 mol) as NMP and 127.12 g (0.464 mol) as NaCl)), 5.62 g of a 48% by weight sodium hydrosulfide aqueous solution (0.048 mol as sodium hydrosulfide) and 5.07 g of a 48% by weight sodium hydroxide aqueous solution (0.061 mol as sodium hydroxide) as the sulfidizing agent (b), 7.07 g (0.048 mol) of p-dichlorobenzene (p-DCB) as the dihalogenated aromatic compound (c) and 573 g (5.78 mol) of NMP as the organic polar solvent (d). The water content included in the raw materials was 5.56 g (0.309 mol), and the volume of the solvent per 1 mol of sulfur content in the reaction mixture was about 2.50 liters. The amount of the arylene unit (equivalent to the total amount of the phenylene unit derived from linear polyphenylene sulfide added as the linear polyarylene sulfide and the phenylene unit tion of this supplementary addition, the reaction proceeded while heating at 250° C. continued for another 1 hour. After decreasing the temperature to 230° C. over about 15 minutes, the process gradually opened the high-pressure valve provided in the upper portion of the autoclave to discharge a vapor mainly made of NMP. The process obtained about 538 g of a liquid component by condensation of this vapor component in a water cooled condenser tube and closed the high-pressure valve to seal the autoclave. The process then rapidly cooled down the autoclave to about room temperature and recovered a reaction product from the autoclave.

<Analytical Evaluation of Reaction Product>

The procedure dispersed part of the obtained reaction product in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 76.2%. The formation rate of cyclic polyphenylene sulfide was 15.9% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 55 kg/(m²·hr).

<Recovery of Cyclic Polyarylene Sulfide>

The procedure placed 100 g of a filtrate component obtained by the same technique as the above evaluation of the solid-liquid separability, in a 300 mL flask and substituted the inside of the flask with nitrogen. The procedure then heated the reaction product to 100° C. and subsequently cooled the reaction product to 80° C., with stirring. Although a partly insoluble component was present at ordinary temperature, no insoluble component was observed in the stage heated to 100° C. and in the stage cooled to 80° C. The procedure then slowly added 33 g of water dropwise with a tube pump over about 15 minutes, while stirring the reaction product at the temperature of 80° C. in the system. The weight ratio of NMP to water in the filtrate mixture after dropwise addition of water was 75 to 25. In the process of addition of water to the filtrate, the temperature of the mixture was decreased to about 75° C. by dropwise addition of water, and a solid content was gradually produced in the mixture. At the stage that dropwise addition of water was concluded, the mixture was a slurry with the solid content dispersed therein. The procedure cooled the slurry to about 30° C. over about 1 hour with stirring, subsequently continued stirring for about 30 minutes at the temperature of not higher than 30° C., and suction-filtered the resulting slurry through a glass filter with apertures of 10 to 16 μm. An operation of dispersing the resulting solid content (including the mother liquid) in about 30 g of water, stirring the dispersion at 70° C. for 15 minutes, and suction-filtering the dispersion through the glass filter in the same manner as above was repeated a total of four times. A dried solid was obtained by treating the resulting solid content at 70° C. in a vacuum dryer for 3 hours.

Analysis of the dried solid by HPLC resulted in detection of cyclic polyphenylene sulfides of the repeating unit numbers of 4 to 15. The content rate of the cyclic polyphenylene sulfide in the obtained dried solid was about 87% by weight, so that the obtained dried solid was identified as high purity cyclic polyphenylene sulfide. The impurity rate of this dried solid was 2.1%.

The reaction mixture was recovered and analyzed at the end of the process 1 when the series of operations was terminated. As the result of analysis, the reaction consumption rate of sodium hydrosulfide was 75.0% at the end of the process 1. This proves that the process 2 was performed after the sulfidizing agent included in the reaction mixture was sufficiently consumed for the reaction.

The results of Example 12 show that the production method of the cyclic polyarylene sulfide of the invention allowed for production of high-quality cyclic polyarylene sulfide having a low impurity content rate at a high yield. These results also indicate the extremely high efficiency of solid-liquid separation of the resulting reaction product in manufacture and the remarkably high productivity.

Example 13

The same series of operations as those of Example 12 were performed, except that the amount of p-DCB was reduced to 6.35 g (0.043 mol) in preparation of the reaction mixture in Example 12 and the amount of p-DCB supplementarily added in the process 2 was increased to 2.47 g (0.017 mol). Accordingly, the amount of the arylene unit per 1 mol of sulfur content in the reaction mixture in the process 1 was 0.98 mol, and the amount of the arylene unit per 1 mol of sulfur content in the reaction mixture in the process 2 was 1.05 mol.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 80.4%. The formation rate of cyclic polyphenylene sulfide was 17.0% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 83 kg/(m²·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 87% by weight. The impurity rate of this dried solid was 1.8%.

The reaction mixture was recovered and analyzed at the end of the process 1 when the series of operations was terminated. As the result of analysis, the reaction consumption rate of sodium hydrosulfide was 78.0% at the end of the process 1. This proves that the process 2 was performed after the sulfidizing agent included in the reaction mixture was sufficiently consumed for the reaction.

The results of Example 13 show that the production method of the cyclic polyarylene sulfide of the invention allowed for production of high-quality cyclic polyarylene sulfide having a low impurity content rate at a high yield even under the condition of the insufficient arylene unit in the reaction mixture relative to the sulfur content at the start of the reaction (process 1). These results also indicate the extremely high efficiency of solid-liquid separation of the resulting reaction product in manufacture and the remarkably high productivity.

Comparative Example 8

The same series of operations as those of Example 12 were performed in the process 1, except that 8.83 g (0.060 mol) of p-DCB was added in preparation of the reaction mixture in Example 12 to adjust the arylene unit to 1.05 mol per 1 mol of sulfur content in the reaction mixture.

The same series of operations as those of Example 1 were performed in the process 2, except that only 60 g of NMP was supplementarily added to the autoclave using the small tank without supplementary addition of DCB in the process 2. While p-DCB was not supplementarily added in the process 2 of Comparative Example 8, the arylene unit per 1 mol of sulfur content in the reaction mixture used in the process 1 was 1.05 mol. The reaction accordingly proceeded under the same condition in the process 2. The amount of arylene unit per 1 mol of sulfur content in the reaction mixture was thus consistently 1.05 mol from the start to the end of the reaction.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 70.0%. The formation rate of cyclic polyphenylene sulfide was 10.8% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 15 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 71% by weight. The impurity rate of this dried solid was 4.5%.

Like Example 12, the reaction mixture was recovered and analyzed at the end of the process 1 when the series of operations was terminated. As the result of analysis, the reaction consumption rate of sodium hydrosulfide was 68.1% at the end of the process 1.

The results of Comparative Example 8 show that the procedure that did not perform supplementary addition of the dihalogenated aromatic compound, which is a preferred characteristic of the present invention, to have a different ratio of the arylene unit to the sulfur content in the reaction mixture in the process 1 from that of the present invention caused the low formation rate of the cyclic polyarylene sulfide and allowed for production of only poor quality cyclic polyarylene sulfide having a very high impurity rate.

Example 14

The same series of operations as those of Example 1 were performed, except that the amount of p-DCB was reduced to 3.53 g (0.024 mol) in preparation of the reaction mixture in Example 1 and the amount of p-DCB supplementarily added in the process 2 was increased to 5.29 g (0.036 mol). Accordingly, the amount of the arylene unit per 1 mol of sulfur content in the reaction mixture in the process 1 was 0.90 mol, and the amount of the arylene unit per 1 mol of sulfur content in the reaction mixture in the process 2 was 1.05 mol.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 17.8%. The formation rate of cyclic polyphenylene sulfide was 17.8% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 80 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 86% by weight. The impurity rate of this dried solid was 2.3%.

The reaction mixture was recovered and analyzed at the end of the process 1 when the series of operations was terminated. As the result of analysis, the reaction consumption rate of sodium hydrosulfide was 77.5% at the end of the process 1. This proves that the process 2 was performed after the sulfidizing agent included in the reaction mixture was sufficiently consumed for the reaction.

The results of Example 14 show that setting the more excess sulfur condition than that of Example 13 to the ratio of the arylene unit to the sulfur content in the reaction mixture at the start of the reaction (process 1) in the production method of the cyclic polyarylene sulfide of the invention further improved the formation rate of the cyclic polyarylene sulfide.

Example 15

The same series of operations as those of Example 14 were performed (the reaction consumption rate of sodium hydrosulfide was 77.5% at the end of the process 1), except that the amount of p-DCB supplementarily added in the process 2 was increased to 7.06 g (0.048 mol). Accordingly, the amount of the arylene unit per 1 mol of sulfur content in the reaction mixture in the process 1 was 0.90 mol, and the amount of the arylene unit per 1 mol of sulfur content in the reaction mixture in the process 2 was 1.10 mol.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 81.0%. The formation rate of cyclic polyphenylene sulfide was 18.2% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 155 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 86% by weight. The impurity rate of this dried solid was 3.7%.

The results of Example 15 show that setting the excess sulfur condition like Example 14 to the ratio of the arylene unit to the sulfur content in the reaction mixture at the start of the reaction (process 1) and setting the higher ratio of the arylene unit than that of Example 14 per 1 mol of sulfur content in the reaction mixture in the process 2 in the production method of the cyclic polyarylene sulfide of the invention enhanced the solid-liquid separability of the resulting reaction product in manufacture of the cyclic polyarylene sulfide and further improved the formation rate of the cyclic polyarylene sulfide, while slightly increasing the impurity rate.

Comparative Example 9

The same series of operations as those of Example 15 were performed in the process 1, except that the heating operation was terminated when the temperature was raised to 200° C.

and the operations of the process 2 were performed subsequently. The reaction consumption rate of sodium hydrosulfide was 29.4% at the end of the process 1 in this case. This indicates that the process 2 was performed prior to sufficient reaction consumption of the sulfidizing agent included in the reaction mixture.

<Analytical Evaluation of Reaction Product>

The procedure dispersed part of the reaction product obtained after the process 2 and the solid-liquid separation in a large excess of water to recover a water-insoluble component and dried the recovered water-insoluble component to obtain a solid content. As the result of structural analysis by infrared spectroscopy, this solid content was identified as a compound consisting of the phenylene sulfide units.

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 80.1%. The formation rate of cyclic polyphenylene sulfide was 12.5% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 310 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 78% by weight. The impurity rate of this dried solid was 5.6%.

The results of Comparative Example 9 show that supplementary addition of the dihalogenated aromatic compound, which is a preferred characteristic of the invention, prior to reaction consumption of 50% or more of the sulfidizing agent, i.e., in the state of insufficient reaction consumption of the sulfidizing agent caused the low formation rate of cyclic polyarylene sulfide and resulted in production of only poor-quality cyclic polyarylene sulfide having the very high impurity rate.

Example 16

The same series of operations as those of Example 15 were performed, except that the reaction temperature was raised to 260° C. in the process 2.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 82.3%. The formation rate of cyclic polyphenylene sulfide was 18.6% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 170 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 87% by weight. The impurity rate of this dried solid was 3.2%.

The results of Example 16 show that the production method of the cyclic polyarylene sulfide of the invention using the linear PAS as the raw material and performing the process 2 at the higher temperature than the process 1 was inclined to enhance the solid-liquid separability of the resulting reaction product in manufacture of the cyclic polyarylene sulfide, improve the content rate of the resulting cyclic polyarylene sulfide and reduce the impurity rate.

Example 17

The same series of operations as those of Example 16 were performed, except that the holding time at 250° C. was extended to 2 hours in the process 1.

<Analytical Evaluation of Reaction Product>

The obtained reaction product and the liquid component recovered by deliquoring operation after the reaction were analyzed by high-performance liquid chromatography and ion chromatography. The result of such analyses shows that the reaction consumption rate of sodium hydrosulfide used as the sulfidizing agent was 90.0%. The formation rate of cyclic polyphenylene sulfide was 19.3% relative to the formation rate on the assumption that the linear polyarylene sulfide and the sulfidizing agent in the reaction mixture were fully converted to cyclic polyphenylene sulfide. As the evaluation result of the solid-liquid separability of the obtained reaction product, the filtration rate was 175 kg/(m$^2$·hr).

A filtrate component obtained by solid-liquid separation as described above was treated in the same manner as recovery of the cyclic polyarylene sulfide in Example 1. Analysis of the resulting dried solid by HPLC resulted in detection of cyclic polyphenylene sulfides of the repeating unit numbers of 4 to 15. The content rate of the cyclic polyphenylene sulfide in the resulting dried solid was about 87% by weight. The impurity rate of this dried solid was 3.1%.

The reaction mixture was recovered and analyzed at the end of the process 1 when the series of operations was terminated. As the result of analysis, the reaction consumption rate of sodium hydrosulfide was 88.6% at the end of the process 1. This proves that the process 2 was performed after the sulfidizing agent included in the reaction mixture was sufficiently consumed for the reaction.

The results of Example 17 show that the enhancement in reaction consumption rate of the sulfidizing agent at the end of the process 1 compared with Example 16 was inclined to improve the formation rate of the cyclic polyarylene sulfide and further reduce the impurity rate.

The invention claimed is:

1. A production method of a cyclic polyarylene sulfide by a reaction of a reaction mixture under heating, wherein the reaction mixture includes at least a sulfidizing agent (a), a dihalogenated aromatic compound (b) and an organic polar solvent (c), the reaction mixture having the organic polar solvent (c) of not less than 1.25 liters and not more than 50 liters relative to 1 mol of sulfur content in the reaction mixture, the production method comprising:
 a process 1 of heating the reaction mixture having an arylene unit of not less than 0.80 mol but less than 1.05 mol per 1 mol of the sulfur content in the reaction mixture and thereby causing the reaction to proceed until 50% or more of the sulfidizing agent (a) in the reaction mixture is consumed for the reaction;
 subsequent to the process 1, a process 2 of further causing the reaction to proceed under heating after addition of the dihalogenated aromatic compound (b) to have the arylene unit of not less than 1.05 mol and not greater than 1.50 mol per 1 mol of the sulfur content in the reaction mixture, so as to obtain a reaction product including at least a cyclic polyarylene sulfide and a linear polyarylene sulfide; and subsequent to the process 2, a process 3 of performing solid-liquid separation of the reaction product in a temperature range of not higher than a boiling point of the organic polar solvent (c) under ordinary pressure, so as to obtain a filtrate including the cyclic polyarylene sulfide and the organic polar solvent (c).

2. The production method of the cyclic polyarylene sulfide according to claim 1, wherein
the process 1 heats the reaction mixture having the arylene unit of not less than 0.80 mol but less than 1.00 mol per 1 mol of the sulfur content in the reaction mixture.

3. The production method of the cyclic polyarylene sulfide according to claim 1, wherein
the reaction mixture further includes a linear polyarylene sulfide (d) as the raw material component.

4. The production method of the cyclic polyarylene sulfide according to claim 3, wherein
the reaction mixture includes the linear polyarylene sulfide (d) as a raw material component at a start of the reaction in the process 1.

5. The production method of the cyclic polyarylene sulfide according to claim 1, wherein
the process 2 is performed after the reaction proceeds until 70% or more of the sulfidizing agent (a) in the reaction mixture is consumed for the reaction in the process 1.

6. The production method of the cyclic polyarylene sulfide according to claim 1, wherein
the process 1 is performed using the reaction mixture containing 0.2 to 20.0 mol of water per 1 mol of the sulfur content in the reaction mixture.

7. The production method of the cyclic polyarylene sulfide according to claim 1, wherein
the reaction mixture is heated at a temperature exceeding a reflux temperature of the reaction mixture under ordinary pressure in the process 1 and in the process 2.

8. The production method of the cyclic polyarylene sulfide according to claim 1, wherein
a pressure in heating the reaction mixture is equal to or more than 0.05 MPa as a gauge pressure in the process 1 and in the process 2.

9. The production method of the cyclic polyarylene sulfide according to claim 1, wherein
the dihalogenated aromatic compound (b) is dichlorobenzene.

10. The production method of the cyclic polyarylene sulfide according to claim 1, wherein
the sulfidizing agent (a) is an alkali metal sulfide.

11. The production method of the cyclic polyarylene sulfide according to claim 3, wherein
the linear polyarylene sulfide (d) used as the raw material component is a linear polyarylene sulfide obtained by separation of a cyclic polyarylene sulfide from a polyarylene sulfide mixture including a cyclic polyarylene sulfide and a linear polyarylene sulfide, wherein the polyarylene sulfide mixture is obtained by a reaction under heating of a reaction mixture, wherein the reaction mixture includes at least a sulfidizing agent (a), a dihalogenated aromatic compound (b) and an organic polar solvent (c) and the reaction mixture has the organic polar solvent (c) of not less than 1.25 liters and not more than 50 liters relative to 1 mol of sulfur content in the reaction mixture, by a method comprising:

a process 1 of heating the reaction mixture having an arylene unit of not less than 0.80 mol but less than 1.05 mol per 1 mol of the sulfur content in the reaction mixture and thereby causing the reaction to proceed until 50% or more of the sulfidizing agent (a) in the reaction mixture is consumed for the reaction; and subsequent to the process 1, a process 2 of further causing the reaction to proceed under heating after addition of the dihalogenated aromatic compound (b) to have the arylene unit of not less than 1.05 mol and not greater than 1.50 mol per 1 mol of the sulfur content in the reaction mixture, so as to obtain a reaction product including at least a cyclic polyarylene sulfide and a linear polyarylene sulfide.

12. The production method of the cyclic polyarylene sulfide according to claim 3, wherein
the linear polyarylene sulfide (d) used as the raw material component is a linear polyarylene sulfide obtained by separation of a cyclic polyarylene sulfide from a polyarylene sulfide mixture including a cyclic polyarylene sulfide and a linear polyarylene sulfide, wherein the polyarylene sulfide mixture is obtained by a reaction under heating of a reaction mixture, wherein the reaction mixture includes at least a linear polyarylene sulfide (d), a sulfidizing agent (a), a dihalogenated aromatic compound (b) and an organic polar solvent (c), and the reaction mixture has the organic polar solvent (c) of not less than 1.25 liters and not more than 50 liters relative to 1 mol of sulfur content in the reaction mixture, by a method comprising:

a process 1 of heating the reaction mixture having an arylene unit of not less than 0.80 mol but less than 1.05 mol per 1 mol of the sulfur content in the reaction mixture and thereby causing the reaction to proceed until 50% or more of the sulfidizing agent (a) in the reaction mixture is consumed for the reaction; and subsequent to the process 1, a process 2 of further causing the reaction to proceed under heating after addition of the dihalogenated aromatic compound (b) to have the arylene unit of not less than 1.05 mol and not greater than 1.50 mol per 1 mol of the sulfur content in the reaction mixture, so as to obtain a reaction product including at least a cyclic polyarylene sulfide and a linear polyarylene sulfide.

* * * * *